(12) United States Patent
Ohlson et al.

(10) Patent No.: US 9,448,243 B2
(45) Date of Patent: Sep. 20, 2016

(54) WEAK AFFINITY CHROMATOGRAPHY

(71) Applicants: Sten Ohlson, Malmoe (SE); Anthony R. Torres, Centerville, UT (US)

(72) Inventors: Sten Ohlson, Malmoe (SE); Anthony R. Torres, Centerville, UT (US)

(73) Assignee: Sten Ohlson, Malmoe (CH)

( * ) Notice: Subject to any disclaimer, the term of this patent is extended or adjusted under 35 U.S.C. 154(b) by 0 days.

(21) Appl. No.: 14/477,695

(22) Filed: Sep. 4, 2014

(65) Prior Publication Data

US 2015/0125877 A1    May 7, 2015

Related U.S. Application Data

(60) Provisional application No. 61/873,709, filed on Sep. 4, 2013.

(51) Int. Cl.
| | |
|---|---|
| *G01N 33/74* | (2006.01) |
| *B01D 15/38* | (2006.01) |
| *G01N 30/72* | (2006.01) |
| *G01N 30/88* | (2006.01) |

(52) U.S. Cl.
CPC ......... *G01N 33/743* (2013.01); *B01D 15/3804* (2013.01); *G01N 30/7233* (2013.01); *G01N 2030/8813* (2013.01); *G01N 2430/00* (2013.01); *G01N 2560/00* (2013.01)

(58) Field of Classification Search
None
See application file for complete search history.

(56) References Cited

U.S. PATENT DOCUMENTS

| | | | | |
|---|---|---|---|---|
| 4,229,537 A | * | 10/1980 | Hodgins et al. | 435/177 |
| 4,546,161 A | * | 10/1985 | Harvey et al. | 527/312 |
| 4,879,247 A | | 11/1989 | Ohlsen | |
| 8,304,248 B2 | | 11/2012 | Torres | |
| 2003/0199671 A1 | * | 10/2003 | Rondon et al. | 530/317 |
| 2005/0029196 A1 | * | 2/2005 | Rhemrev-Boom | 210/656 |
| 2008/0293587 A1 | | 11/2008 | Ohlson et al. | |
| 2009/0068179 A1 | * | 3/2009 | Nayeri et al. | 424/133.1 |

FOREIGN PATENT DOCUMENTS

| | | |
|---|---|---|
| WO | WO 96/16332 A1 | 5/1996 |
| WO | WO 2007/050032 A1 | 5/2007 |

OTHER PUBLICATIONS

Neurath et al. PNAS 1974 vol. 71, p. 2663-2667.*
Brne et al. J. Chromatography (A) 2009 vol. 1216, p. 2658-2663.*
Ruhn et al. J. Chromatography (A) 1994 vol. 669, p. 9-19.*
Moser et al. Bioanalysis 2010 vol. 2, p. 769-790.*
Albumin-Blood (Serum); PubMed Health, National Library of Medicine; Feb. 13, 2013, pp. 1-2; A.D.A.M., Inc.; Atlanta, Georgia.
Bergström et al.; "Elucidating the selectivity of recombinant forms of *Aleuria aurantia* lectin using weak affinity chromatography"; J. Chromatogr. B 885-886, Dec. 2012; pp. 66-72.
Duong-Thi et al.; "High-Throughput Fragment Screening by Affinity LC-MS"; Journal of Biomolecular Screening; Published online Sep. 13, 2012; Society for Laboratory Automation and Screening; pp. 1-12.
Duong-Thi et al.; "Weak Affinity Chromatography as a New Approach for Fragment Screening in Drug Discovery"; Analytical Biochemistry (Feb. 2011), 39 pages.
Landström et al.; "Combining weak affinity chromatography, NMR spectroscopy and molecular simulations in carbohydrate—lysozyme interaction studies"; Org. Biomol. Chem.; 2012; (10); pp. 3019-3032.
Ohlson et al.; "Toward high-throughput drug screening on a chip-based parallel affinity separation platform"; J. Sep. Sci. (2010), 33, pp. 2575-2581.
Ohlson et al.; "Use of monoclonal antibodies for weak affinity chromatography"; Journal of Chromatography A, 758 (1997), pp. 199-208.
Ohlson; "Designing transient binding drugs: A new concept for drug discovery"; Drug Discovery Today; vol. 13, Nos. 9/10; May 2008; pp. 433-439; Sweden.
PCT Application No. PCT/US14/54133; Filing date Sep. 4, 2014; Sten Ohlson; International Search Report mailed Dec. 24, 2014.
SIGMA; Beta-Estradiol; Product Information Sheet, Sigma Product No. E8875; Mar. 30, 1997; 2 pages.
Strandh et al.; "Methods in Molecular Biology, vol. 147: Affinity Chromatography: Methods and Protocols"; Chapter 2: Weak Affinity Chromatography; Apr. 2000; pp. 7-23.

* cited by examiner

Primary Examiner — Jacob Cheu
(74) Attorney, Agent, or Firm — Thorpe North & Western LLP

(57) ABSTRACT

The present invention provides methods for analyzing a target compound from a biological sample. In one aspect, a method for analyzing a target compound in a biological sample can comprise delivering a biological sample through an affinity column, the affinity column having a binding ligand coupled to a stationary structural support, wherein the affinity column has a high density of the binding ligand per the stationary structural support and wherein the binding ligand has been preselected to cause weak affinity separation zonal retardation of the target compound from the biological sample forming a target compound fraction and a biological sample fraction and detecting the target compound by mass spectrometry.

18 Claims, 29 Drawing Sheets

WEAK AFFINITY CHROMATOGRAPHY

PRIORITY CLAIM

Priority is claimed to U.S. Provisional Patent Application Ser. No. 61/873,709 filed Sep. 4, 2013, which is hereby incorporated herein by reference in its entirety.

FIELD OF THE INVENTION

The present invention relates to the analysis of a target compound from a biological sample. Accordingly, the present invention involves the fields of medical and clinical diagnostics.

BACKGROUND OF THE INVENTION

There are many instances where target compounds in a biological sample need to be detected and analyzed. For example, in diagnostic laboratories, it is necessary to detect the presence of particular compounds, such as steroids, in biological samples such as a blood or urine sample. In another example, the presence and/or concentration of particular compounds, again such as steroids, in particular biological samples, such as blood samples, can be a diagnostic indicator of possible disease states in a patient. Further, the current research into the use of disease markers to diagnose possible disease states in patients is identifying many specific molecules whose presence in particular biological samples may indicate the presence of a particular disease states in a patient. Therefore, it is necessary to be able to detect and analyze these target compounds in biological samples as directly as possible.

In connection with blood samples, blood serum, which often contains the target compounds and often is used as the biological blood sample for diagnostic and testing purposes, presents challenges for the physical detection of target compounds. This is because the target compounds are present in the sample at substantially lower concentrations as compared to other molecules. Proteins/peptides in particular can cause interference problems with many current separation methods. With current separation and analysis methods, some or all of these proteins are removed from the serum prior to determining whether or not the target compounds are present. Thus, current analysis methods usually require two or more separation methods to be able to identify a target compound present in the complex mixture of compounds present in serum and other biological samples. The method describes a way to measure molecules directly from whole serum by weak-affinity liquid chromatography-mass spectrometry.

SUMMARY OF THE INVENTION

The present invention provides methods for separating target compounds from biological samples. In one aspect, for example, a method for analyzing a target compound in a biological sample can comprise delivering a biological sample through an affinity column, the affinity column having a binding ligand coupled to a stationary structural support, wherein the affinity column has a high density of the binding ligand per the stationary structural support and wherein the binding ligand has been preselected to cause weak affinity separation zonal retardation of the target compound from the biological sample forming a target compound fraction and a biological sample fraction and detecting the target compound. In one aspect, detection can be by mass spectrometry.

Various biological samples are contemplated for use with the methods according to aspects of the present invention. For example, in one aspect, the biological sample can be a biological fluid. Non-limiting examples of biological fluids can include blood serum, blood plasma, urine, CNS fluid, saliva, cellular extracts, tissue culture extracts, and mixtures thereof. Additionally, the biological sample can be utilized in a variety of forms. For example, in one aspect the biological sample is an undiluted biological fluid. In another aspect, the biological sample is a non-dialyzed biological fluid. In yet another aspect, the biological sample is a non-ultrafiltrated biological fluid. Furthermore, a biological sample can be treated prior to separation. Non-limiting examples of such treatments include reducing agents, protease enzyme treatments, carbohydrate modifications, detergents, urea, and combinations thereof.

In some embodiments, the biological sample can contain additional binding ligands. The high density of binding ligands of the affinity column can be sufficient to cause weak affinity separation zonal retardation when the biological sample contains additional binding ligands. In one aspect, the binding ligand can have a density of at least 25 mg/g binding ligand per the stationary structural support.

The methods of the present invention can be used to process large amounts of biological sample as compared to the capacities of the affinity columns being utilized. In one aspect, for example, the affinity column can have a binding capacity that is at least the same as the total target compound in an undiluted biological sample.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

Additional features and advantages of the invention will be apparent from the detailed description which follows, taken in conjunction with the accompanying drawings, which together illustrate, by way of example, features of the invention.

DETAILED DESCRIPTION

Figure 1:
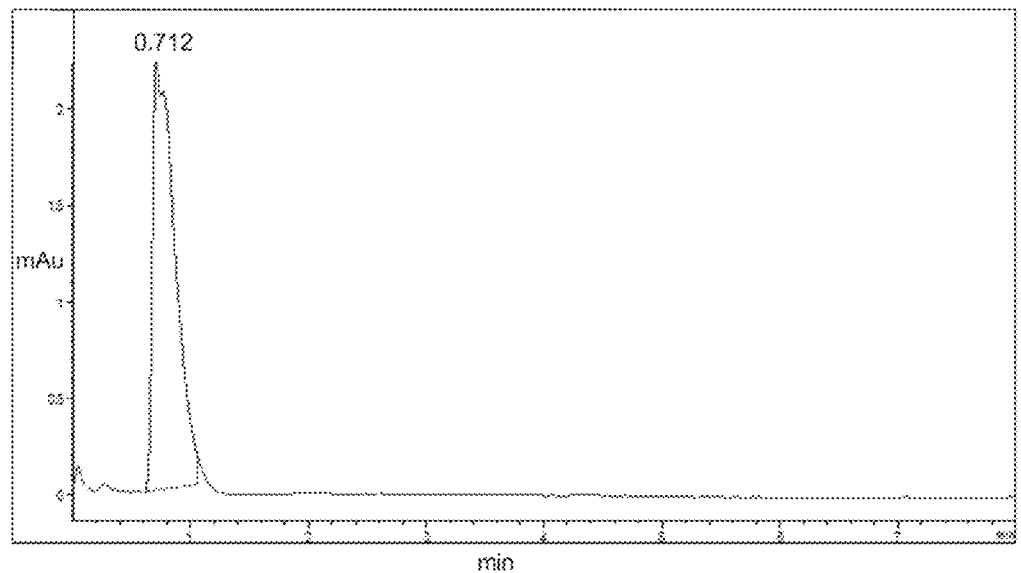
FIG. 1 is a chromatogram of ethanol run through a column without binding ligands according to one aspect of the present invention.
Figure 2:
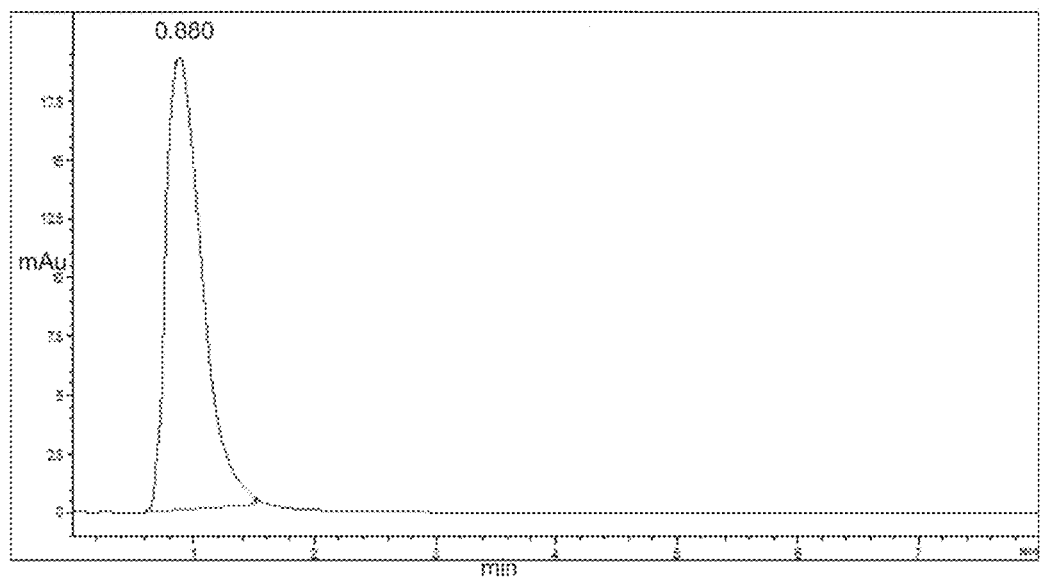
FIG. 2 is a chromatogram of 100 ng cortisone run through a column without binding ligands according to one aspect of the present invention.
Figure 3:
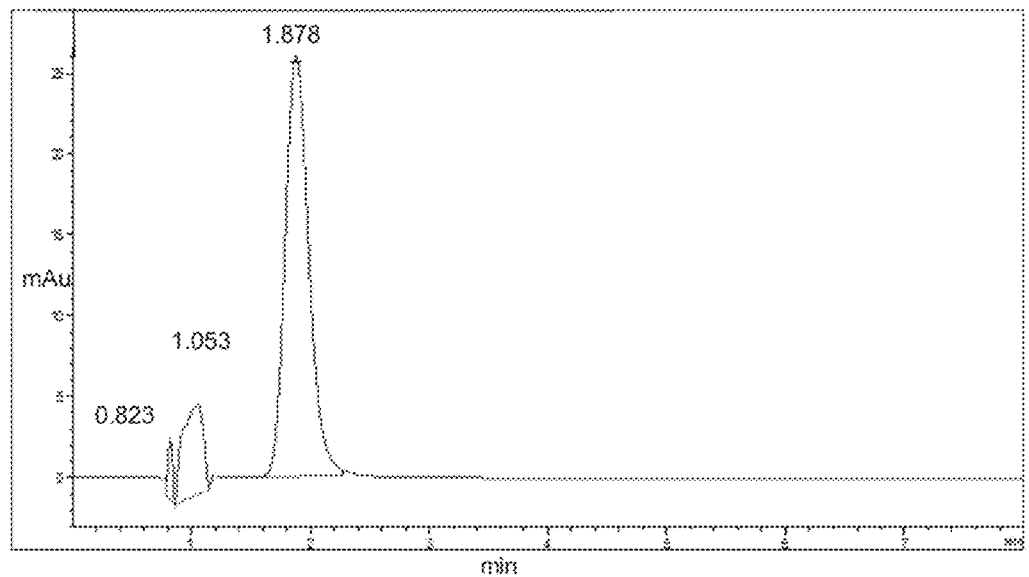
FIG. 3 is a chromatogram of 100 ng of cortisone run through an albumin column according to one aspect of the present invention.

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "a binding ligand" includes one or more of such binding ligands, and reference to "the column" includes reference to one or more of such columns.

DEFINITIONS

In describing and claiming the present invention, the following terminology will be used in accordance with the definitions set forth below.

As used herein, the term "biological sample" generally refers to bodily substances, such as tissues and fluids, removed from a subject.

As used herein, "subject" refers to a mammal that may benefit from aspects of the present disclosure. Examples of subjects include humans, and may also include other animals such as horses, pigs, cattle, dogs, cats, rabbits, and aquatic mammals.

As used herein, the term "affinity binding" refers to binding between a ligand and a biomolecule.

As used herein, the term "binding capacity," when referring to an affinity column, refers to the amount of biological material that is capable of binding to the column.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of"

an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Invention

General chromatography techniques rely on chemical interactions for the separation of complex mixtures. The introduction of High Performance Liquid Affinity Chromatography (HPLAC) signified an optimization of the affinity technique, primarily with regard to speed and resolution. However, in comparison with other types of chromatography such as, for example, hydrophobic or ion exchange chromatography it appeared that the efficiency of HPLAC was approximately ten times lower than that of traditional HPLC. The use of more effective carrier material in affinity chromatography such as small-size particles can increase the performance up to a level determined by the molecular interaction per se between the substance and the complementary ligand.

Contrary to traditional affinity chromatography techniques with adsorption followed by elution by changing the conditions in some way, the weak affinity chromatography makes use of a separation technique where highly reversible weak interactions are used to bind the substance under no or minor change of conditions.

It has been discovered that weak affinity chromatography techniques can be used to specifically analyze discrete target compounds from biological samples. In one embodiment, a column can be manufactured having a binding ligand coupled to a stationary structural support, wherein the binding ligand has been preselected to cause weak affinity separation zonal retardation of the target compound from the biological sample forming a target compound fraction and a biological sample fraction. Such a method can also include detecting and quantifying the compound. This process can produce a meaningful separation between the target compound and the biological sample to facilitate detection.

Accordingly, in one aspect, a method for analyzing a target compound in a biological sample can include delivering a biological sample through an affinity column, the affinity column having a binding ligand coupled to a stationary structural support, wherein the affinity column has a high density of the binding ligand per the stationary structural support and wherein the binding ligand has been preselected to cause weak affinity separation zonal retardation of the target compound from the biological sample forming a target compound fraction and a biological sample fraction and detecting the target compound. In one aspect, detection can be by mass spectrometry. In one specific aspect, the mass spectrometry detection (MSD) can include electrospray injection (ESI)—atmospheric pressure chemical ionization (APCI) and selective ion monitoring (SIM) that, when coupled to the present weak affinity columns, can provide a powerful identification and quantification technique for analyzing discrete target compounds from a biological samples.

The present binding ligands are bound to a stationary structural support as is known in the chromatography arts. Such stationary structural support can comprise various materials including inorganic materials such as glass or silica and organic materials such as polymeric materials. The present binding ligands can be matched to a target compound of interest such that the interactions between the target compound and the binding ligand produce sufficient zonal retardation of the target compound to allow analysis without impacting the efficiency of the column throughput. As such, a variety of binding ligands can be used depending upon the target compound, and any such binding ligand is considered to be within the present scope. In one embodiment, the binding ligand can be a protein. Non-limiting examples of binding ligands can include transferrin, immunoglobulin, albumin, fibrinogen, orosomucoid, and the like, including mixtures thereof. In one specific aspect, the binding ligand can be albumin. Generally, the binding ligand is coupled to the structural support material at a high density. In one example, the high density can be at least 25 mg/g of binding ligand per the stationary structural support. In various aspects, the density can be at least 50 mg/g, 75 mg/g, or even 100 mg/g. In one specific aspect, the density can be at least 150 mg/g.

A variety of biological samples are contemplated for use with the methods according to aspects of the present invention. For example, in one aspect, the biological sample can be a biological fluid. Non-limiting examples of biological fluids can include blood serum, blood plasma, urine, CNS fluid, saliva, cellular extracts, tissue culture extracts, and mixtures thereof. Such biological samples can be extracted from a subject and made available for analysis according to the methods of the present disclosure. Additionally, the biological sample can be utilized in a variety of forms. For example, in one aspect the biological sample can be an undiluted biological fluid. In another aspect, the biological sample can be a non-dialyzed biological fluid. In yet another aspect, the biological sample can be a non-ultrafiltrated biological fluid. Furthermore, a biological sample can be treated prior to separation. Non-limiting examples of such treatments include reducing agents, protease enzyme treatments, carbohydrate modifications, detergents, urea, and the like, including combinations thereof.

In some embodiments, the biological sample can contain additional binding ligands. In this aspect, the binding ligands are in addition to the binding ligands coupled to the stationary support structure of the column. Such binding ligands remain unbound and flow through the column along with the other components of the biological sample. In this case, the coupled binding ligands can compete with the unbound binding ligands found in the biological sample for interaction with the target compound. Thus, the density of binding ligands should be at high density in order to cause weak affinity separation zonal retardation over the competing interactions. As such, in some cases the high density of binding ligands of the affinity column can be sufficient to cause weak affinity separation zonal retardation when the biological sample contains additional binding ligands. In one specific example, the biological compound can be undiluted blood serum, the target compound can be a steroid, and the binding ligand can be albumin. In this example, the albumin can be present in the biological sample in unbound form as well as coupled to the structural support of the column. Such additional binding ligands in the biological sample can be present in an amount ranging from about 1 g/dL to about 10 g/dL. In one aspect, the additional binding ligands can be present in an amount ranging from about 3 g/dL to about 6 g/dL.

The target compound can be any compound of interest. In one embodiment, the target compound can be a discrete compound of interest found in biological samples. In one aspect, the target compound can be a biological compound. For example, such a biological compound can include naturally occurring biological compounds found in a human subject or a biological compound specifically injected, ingested, or otherwise found in a human subject, e.g. drugs. In one example, the target compound can be a small molecule having a molecular weight of less than 500. In another example, the target compound can be a steroid.

In one aspect, the steroid can include cortisone, hydrocortisone, prednisone, prednisolone, adrenal steroids, estradiol, testosterone, secosteroids, vitamin D derivatives, and mixtures thereof. The target compound can be present in biological sample in varying amounts. In one example, the target compound can be present in the biological sample in an amount ranging from about 0.001 µg/l to about 100 µg/l. In one aspect, the target compound can be present in the biological sample in an amount ranging from about 0.1 µg/l to about 100 µg/l.

In some aspects, the methods of the present invention can be used to process large volumes of biological sample as compared to the capacities of the affinity columns being utilized. In one aspect, for example, the affinity column can have a binding capacity that is at least the same as the total target compound in an undiluted biological sample. As such, when the target compound is present in an low amounts, e.g. 1 wt %, large amounts of biological sample can be processed before the column has reached capacity.

In yet another aspect of the present invention, a system for analyzing a target compound in a biological sample can comprise the biological sample, the biological sample containing the target compound; an affinity column having a binding ligand coupled to a stationary structural support, where the affinity column has a high density of the binding ligand per the stationary structural support and wherein the binding ligand has been preselected to cause weak affinity separation zonal retardation of the target compound from the biological sample forming a target compound fraction and a biological sample fraction; and a detector operatively coupled to the affinity column, the detector configured to detect the target compound and quantify the amount of target compound detected.

The present method generally includes delivering a biological sample, e.g. mixture of proteins, through an affinity column at a specific pH. Such concentration can vary and is generally optimized for the sample, target compound, and column combination used. In one aspect, for example, the pH can be from about 0.0 to about 10.0. In another aspect, the pH can be from about 6.0 to about 7.5. In yet another aspect, the pH can be from about 2.0 to about 6.0.

One benefit of the present techniques for target compound separation from a biological sample is the ability to process biological samples via affinity chromatography that contain high concentrations of proteins and other biological material. In traditional chromatography techniques, a biological sample is generally heavily diluted and/or filtered in order to reduce the protein concentration in the sample to a level that allows all of the protein to bind to the column. The present methods allow high concentration (i.e. undiluted) biological mixture to be processed via weak affinity chromatography in order to ascertain the presence of a target compound of interest, separate such a compound from the biological sample, quantify the amount of target compound present in the biological sample, etc. It should be noted that the addition of column buffer to a protein mixture should not necessarily be considered dilution. For example, a 5 ml whole serum sample processed on a column is not considered "diluted" by the addition of 5 ml of column buffer to facilitate movement through the column because 5 ml of serum is still loaded on the column regardless of the buffer.

It can be beneficial, however, to remove from biological samples tissue, cells, or other large biological matter that can hamper the weak affinity process. Biological samples derived from blood, for example, can be allowed to clot to remove blood cells therefrom. It should be noted, however, that the present scope should not be limited to undiluted biological fluids, and that some level of dilution may be beneficial, depending on the specific affinity columns and the target compounds being separated.

As discussed herein, the biological sample can be a non-dialyzed biological fluid. Such biological fluids can be processed according to the present techniques in a non-dialyzed, a substantially non-dialyzed, or a dialyzed state. Traditional approaches to some chromatography, e.g., ion-exchange, exhaustively dialyze a biological sample such as serum prior to processing. The present techniques allow a biological fluid to be processed at physiological salinity levels. Of course, the salinity can be increased or decreased relative to physiological conditions, depending on the target compound of interest and the biological sample being used, as well as the particular protocol being performed. It should also be noted that in some aspects the biological fluid can be dialyzed.

As discussed herein, the biological sample can be a non-ultrafiltrated biological fluid. Ultrafiltration is known in the art, and is a technique that is typically used in traditional chromatography approaches. The present techniques allow the processing of biological samples that have not been filtered to such an extent, and thus can allow for more efficient processing. It should be noted, however, that the present scope also includes the processing of biological samples that have been substantially non-ultrafiltrated, as well as those that have been ultrafiltrated. Additionally, as is discussed above, it can be beneficial to remove cellular material, tissue, and other debris from the biological sample in order to avoid clogging the column. Such a removal can be accomplished by filtration of the biological sample, and such filtration should not be seen as ultrafiltration.

A biological sample such as a biological fluid can additionally be treated prior to or during chromatography in order to modify a protein or other biological material contained therein. Such modifications can be used to enhance the separation procedure, to facilitate future processing steps to be performed on proteins of interest, to facilitate target identification, and the like. Non-limiting examples of such treatments can include reducing agents, protease enzyme treatments, detergent addition, urea, carbohydrate modifications, and the like.

EXAMPLES

Example 1

Column Preparation

Four columns were prepared, a blank diol-silica column (column A) having no binding ligands and 3 columns (columns B, C, D) loaded with albumin as the binding ligand. Column B was a silica packed column (7 µm, 300 Å porosity) loaded with 96% purity bovine serum albumin (BSA) at a concentration of 66 mg of BSA per gram of silica. Column C was a silica packed column (7 µm, 300 Å porosity) loaded with 99% purity bovine serum albumin (BSA) at a concentration of 77 mg of BSA per gram of silica. Column D was a silica packed column (7 µm, 300 Å porosity) loaded with 99% purity human serum albumin (HSA) at a concentration of 118 mg of HSA per gram of silica. All four column dimensions were 2.1×50 mm stainless steel. Immobilization of the ligands was performed batchwise with periodate activation. 0.5 g of diol-silica was used with 5 ml of $H_2O$ added. The silica was sonicated for 2 minutes, and 0.5 g of periodic acid was added to convert the diol groups to aldehyde-groups. After 2 hours of mixing, the aldehyde-silica was washed with 100 mM phosphate, pH 7.0. 5 ml of the respective ligand in 100 mM phosphate buffer, pH 7.0, was prepared. Ligand concentration was 10 mg/ml. 250 µl $NaCNBH_3$, concentration of 0.1 mg/ml, was added. Coupling time was 40 hours at room temperature (22° C.) on mixing table.

As such four different columns were made:
A Blank column, untreated diol-Silica, packing pressure 300 Bar.
B BSA-column, 96% purity of BSA. Yield, 66%, Lig.density, 66 mg/g Silica.
C BSA-Column, 99% purity of BSA. Yield, 78%, Lig.density, 77 mg/g Silica
D HSA-Column, 99% purity of HSA. Yield, 79%, Lig.density, 118 mg/g Silica.

Example 2

Steroid Detection

Four steroids, cortisone, hydrocortisone, prednisone, and prednisolone were tested on columns A-D of Example 1. The system comprised the columns used in an Agilent 1200-LC-MS system. The steroids were all dissolved in ethanol at a concentration of 0.05 µg/µl. 2 µl samples were run in duplicate. Solvent buffers used included phosphate buffered saline (PBS) at pH 7.4 and 5 mM ammonium-acetate (Am-Ac) salt, pH 6.9. Column temperature was 20° C. with a flow rate of 0.400 ml/min. Detection included the use of UV diode-array detector (DAD) at 237 nm.

The columns were tested with the PBS buffer and the Am-Ac listed above. The capacity factor (k') and dissociation constant (Kd) were determined as set forth in U.S. Pat. No. 4,879,247 issued on Nov. 7, 1989 to Sten Ohlson, which is hereby incorporated by reference in its entirety. The results are listed in Tables 1-4.

TABLE 1

| | k' for PBS buffer | | | |
|---|---|---|---|---|
| Steroid | Column A | Column B | Column C | Column D |
| Cortisone | 0.24 | 1.14 | 1.29 | 2.54 |
| Hydrocortisone | 0.21 | 1.05 | 1.20 | 1.77 |
| Prednisone | 0.22 | 1.07 | 1.23 | 1.74 |
| Prednisolone | 0.22 | 1.27 | 1.41 | 1.64 |

TABLE 2

| | k' for Am-Ac buffer | | | |
|---|---|---|---|---|
| Steroid | Column A | Column B | Column C | Column D |
| Cortisone | 0.15 | 1.03 | 1.19 | 2.71 |
| Hydrocortisone | 0.15 | 0.96 | 1.11 | 1.88 |
| Prednisone | 0.15 | 1.01 | 1.17 | 1.78 |
| Prednisolone | 0.15 | 1.13 | 1.34 | 1.56 |

TABLE 3

| | Kd (µM) for PBS buffer | | |
|---|---|---|---|
| Steroid | Column B (µM) | Column C (µM) | Column D (µM) |
| Cortisone | 256 | 238 | 391 |
| Hydrocortisone | 277 | 257 | 223 |
| Prednisone | 274 | 250 | 516 |
| Prednisolone | 230 | 216 | 602 |

TABLE 4

| | Kd (µM) for Am-Ac buffer | | |
|---|---|---|---|
| Steroid | Column B (µM) | Column C (µM) | Column D (µM) |
| Cortisone | 281 | 255 | 343 |
| Hydrocortisone | 281 | 274 | 503 |
| Prednisone | 288 | 260 | 523 |
| Prednisolone | 257 | 227 | 596 |

A k' between 1 and 10 and Kd greater than 1 µM are generally acceptable for a weak affinity chromatography process. Notably, the present columns provided acceptable characteristics for the detection of steroids using weak affinity columns.

Example 3

Elution Time of Serum

Figure 4:
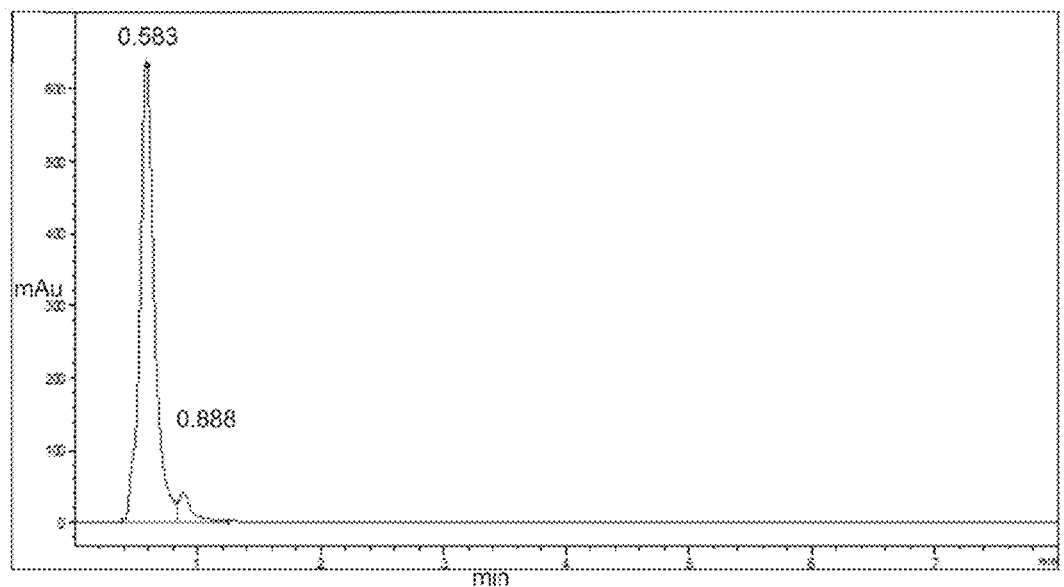
FIG. 4 is a chromatogram of n-serum run through an albumin column according to one aspect of the present invention.
Figure 5:
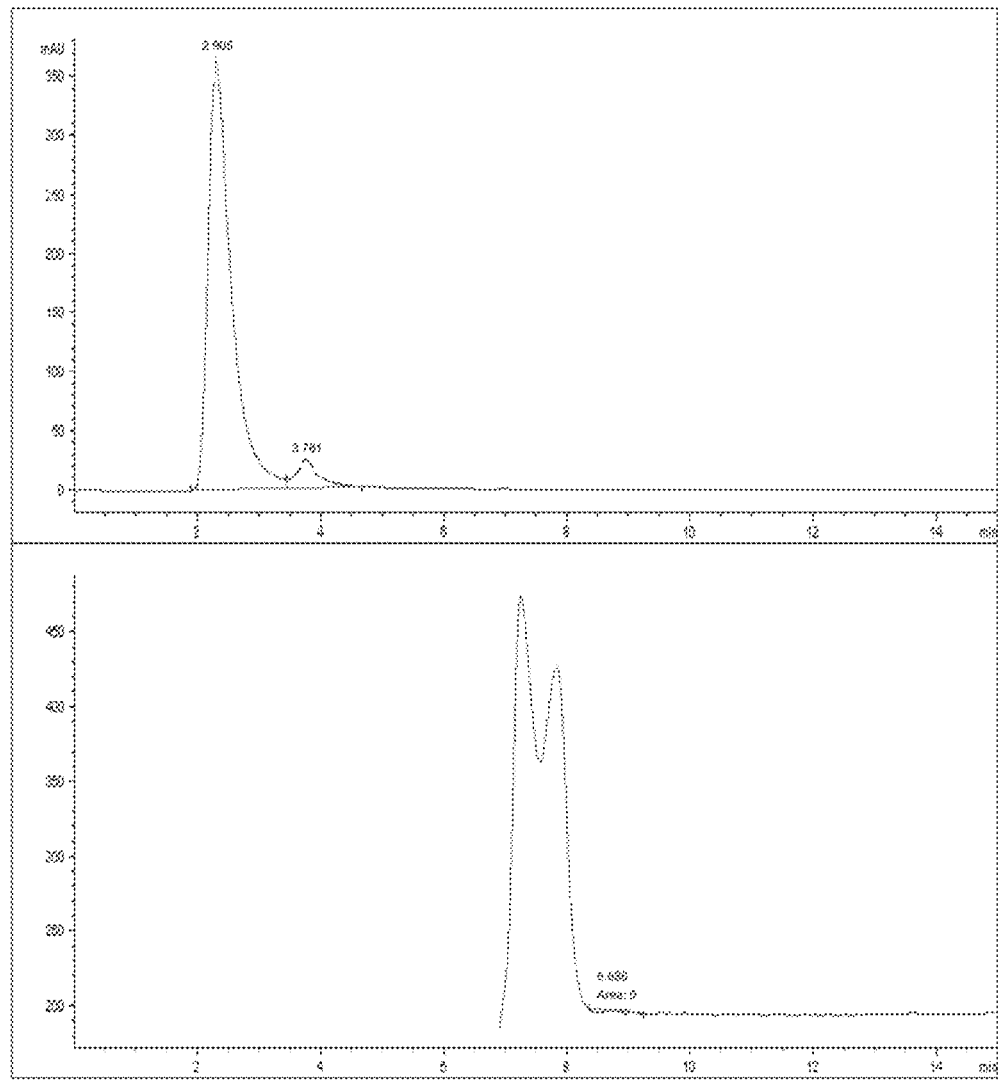
FIG. 5 is a chromatogram of n-serum (diluted 1:5 in a solvent buffer) run through an albumin column according to one aspect of the present invention.
Figure 6:
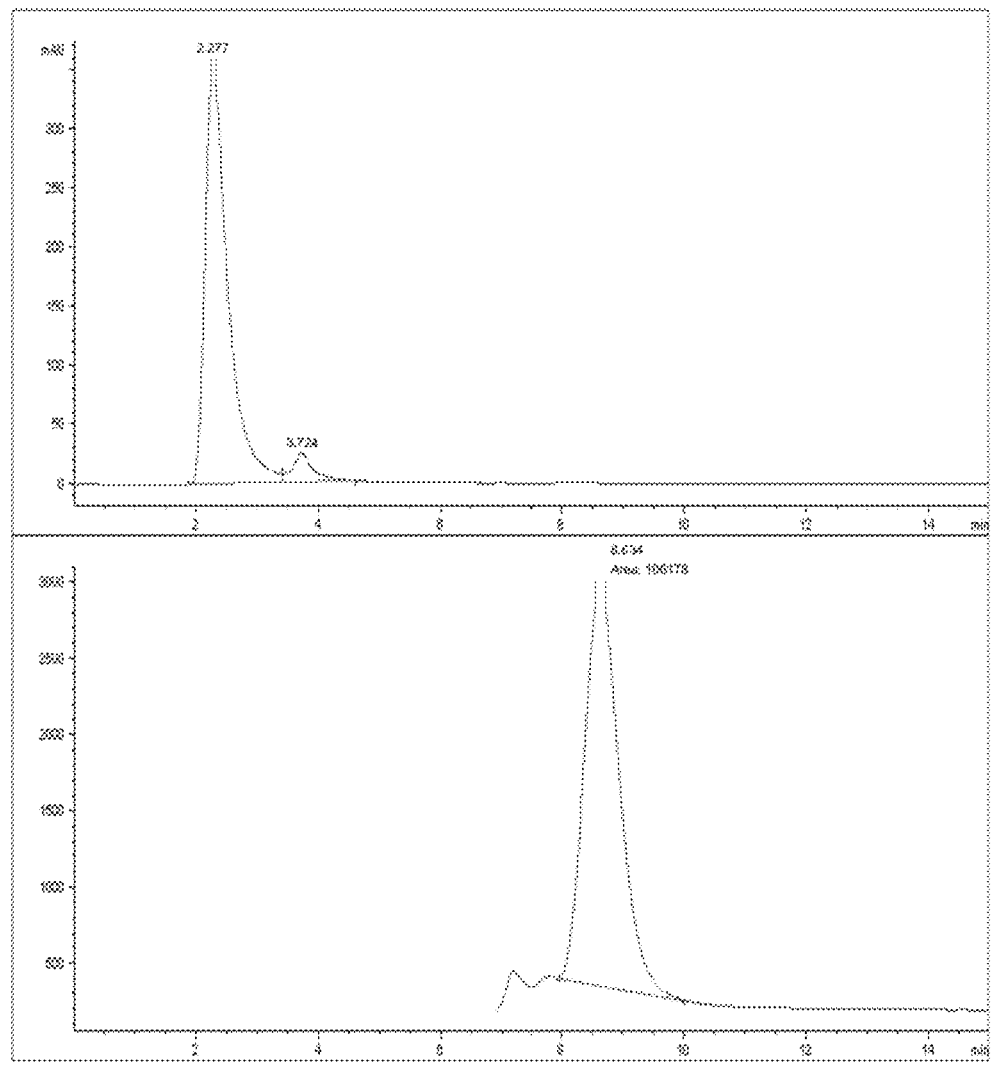
FIG. 6 is a chromatogram of cortisone in serum (2.5 ng/µl) run through an albumin column according to one aspect of the present invention.
Figure 7:
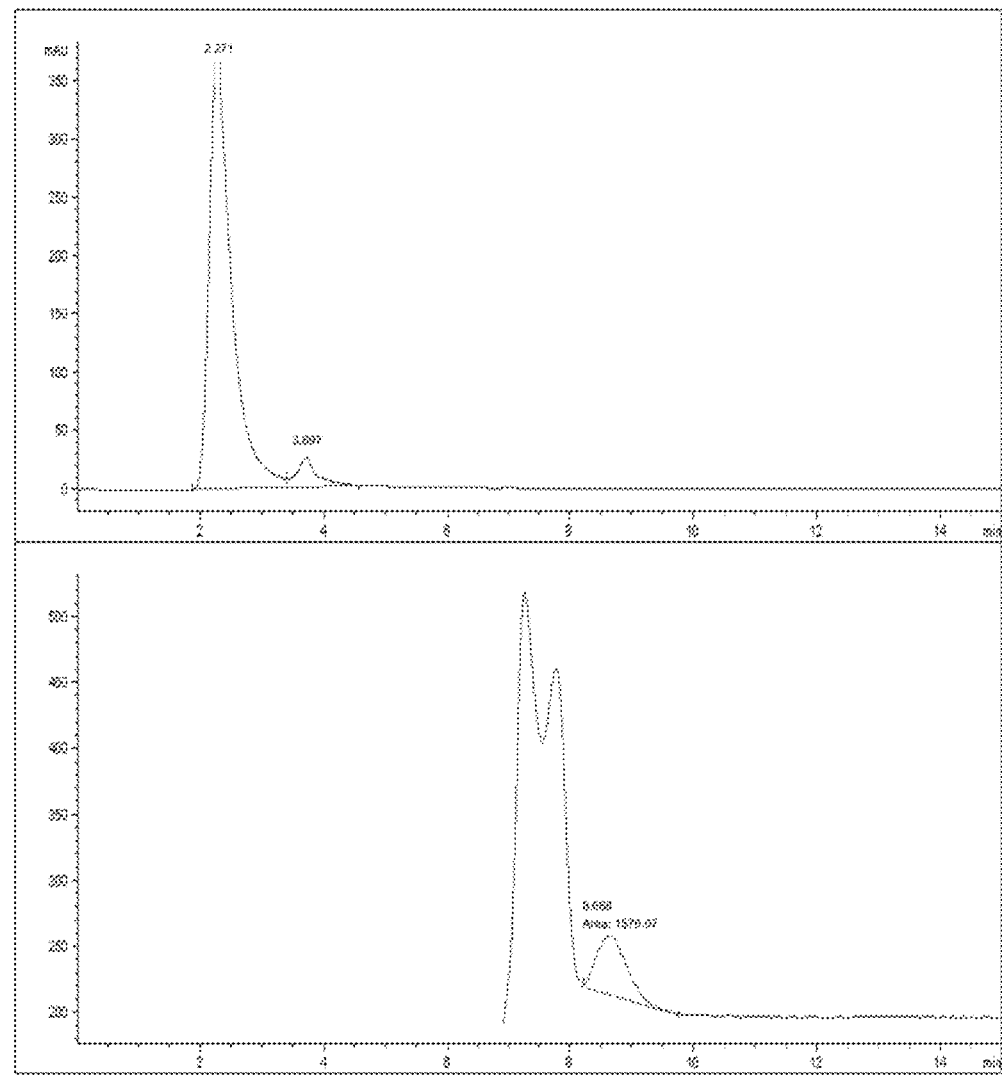
FIG. 7 is a chromatogram of cortisone in serum (0.05 ng/μl) run through an albumin column according to one aspect of the present invention.
Figure 8:
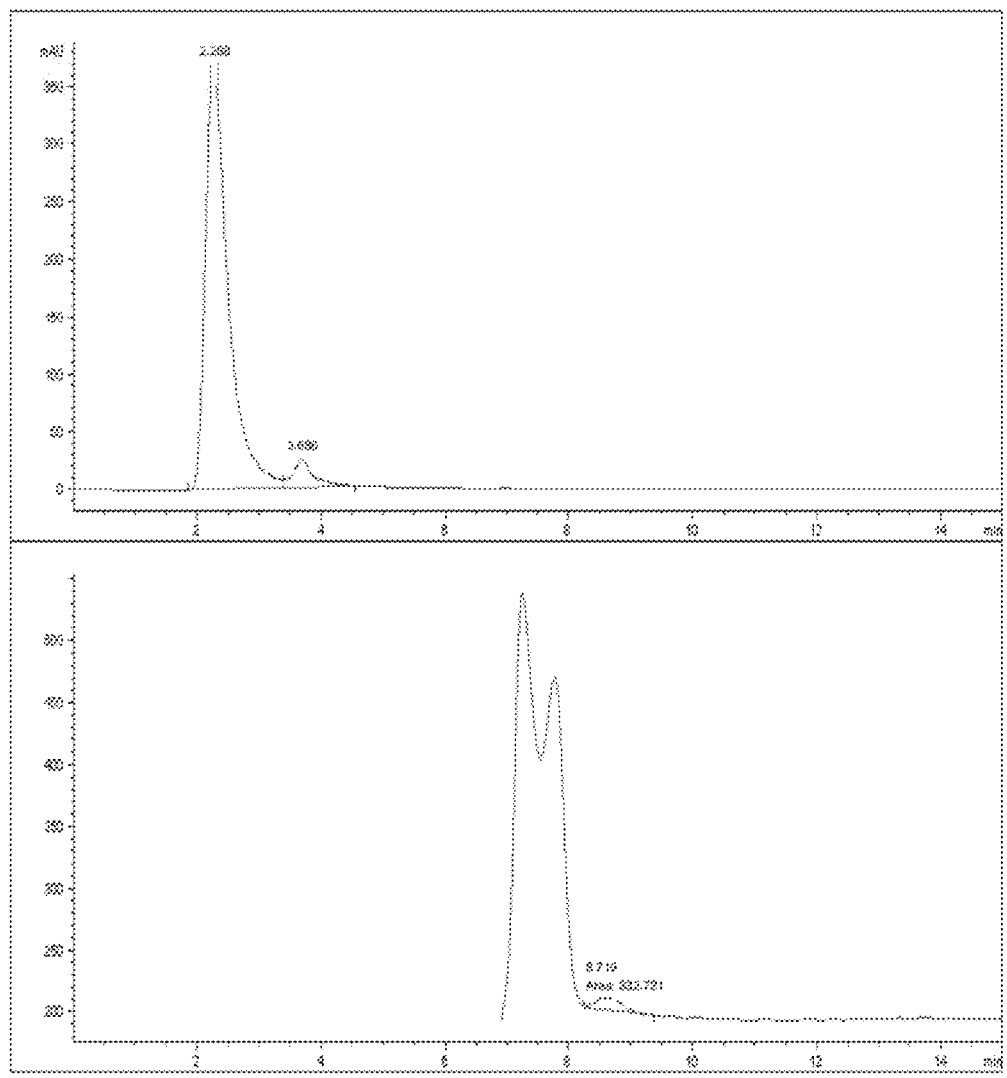
FIG. 8 is a chromatogram of cortisone in serum (0.01 ng/μl) run through an albumin column according to one aspect of the present invention.
Figure 9:
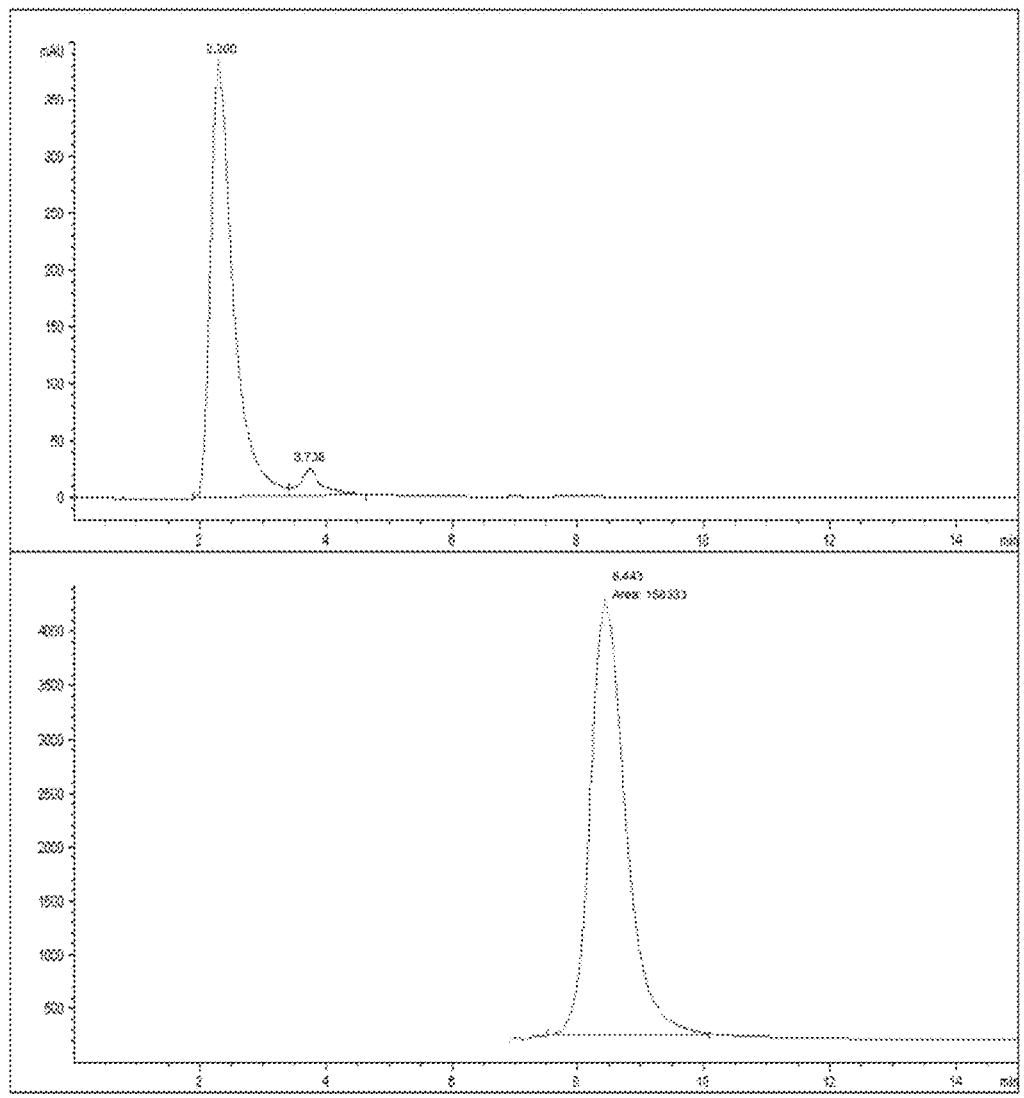
FIG. 9 is a chromatogram of hydrocortisone in serum (2.5 ng/μl) run through an albumin column according to one aspect of the present invention.
Figure 10:
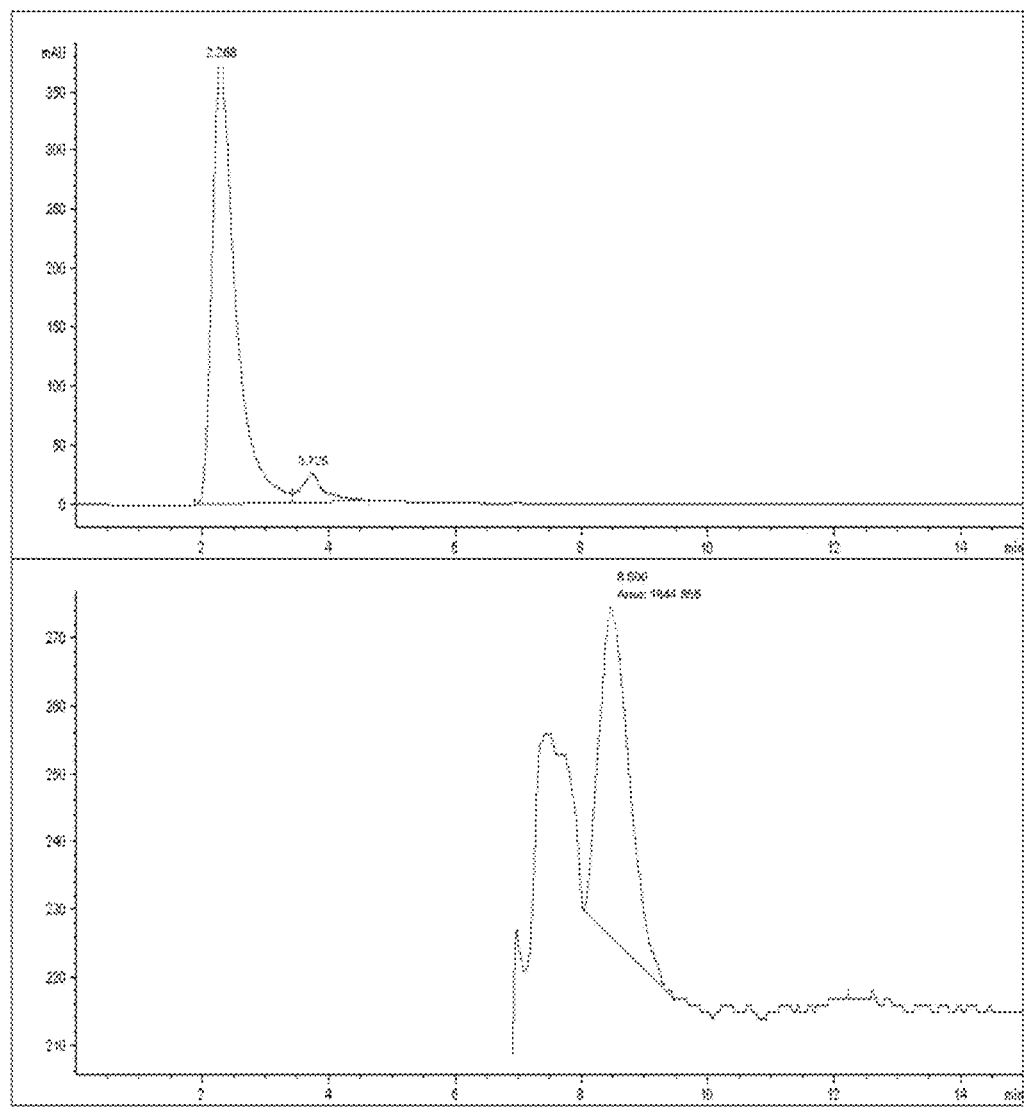
FIG. 10 is a chromatogram of hydrocortisone in serum (0.05 ng/μl) run through an albumin column according to one aspect of the present invention.
Figure 11:
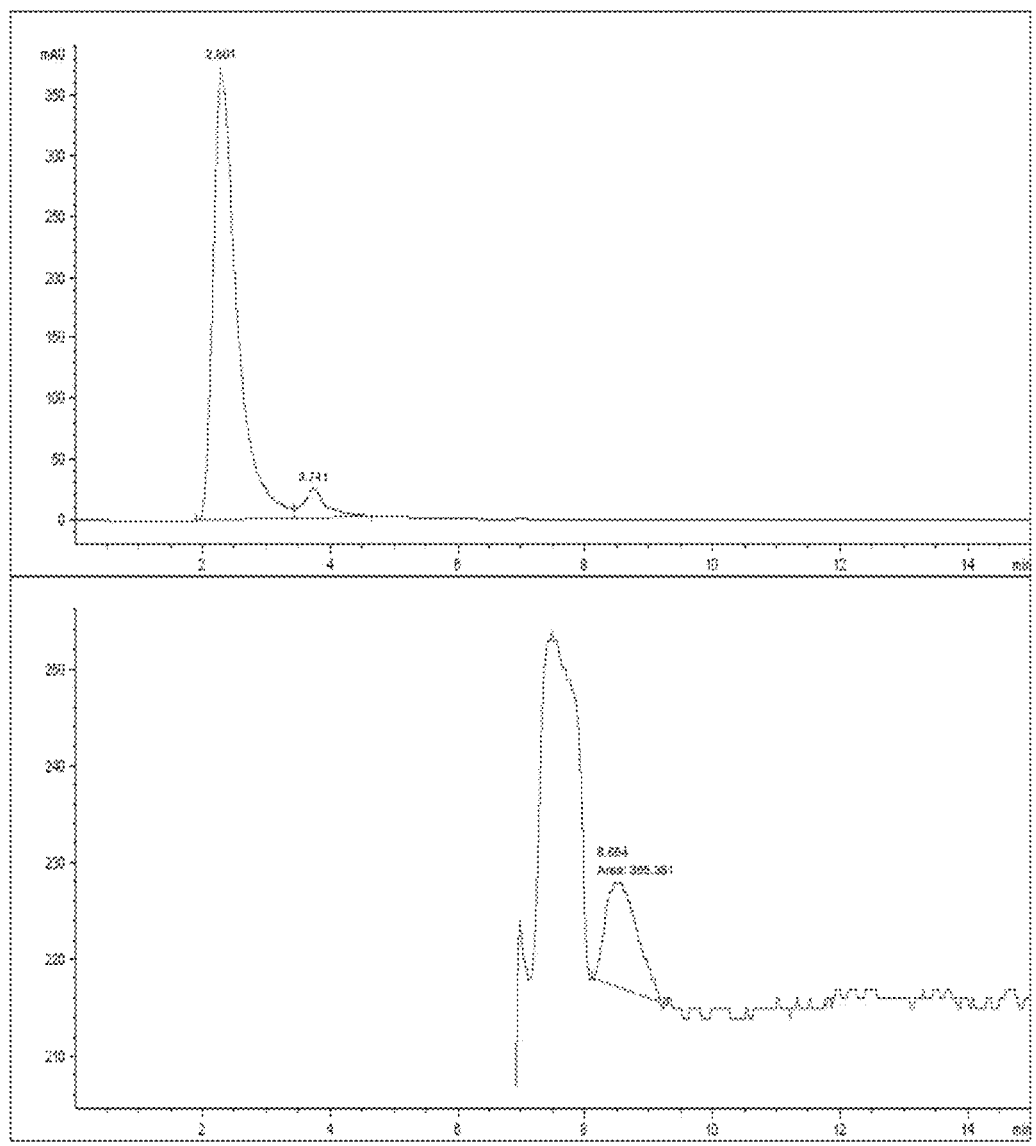
FIG. 11 is a chromatogram of hydrocortisone in serum (0.01 ng/μl) run through an albumin column according to one aspect of the present invention.
Figure 12:
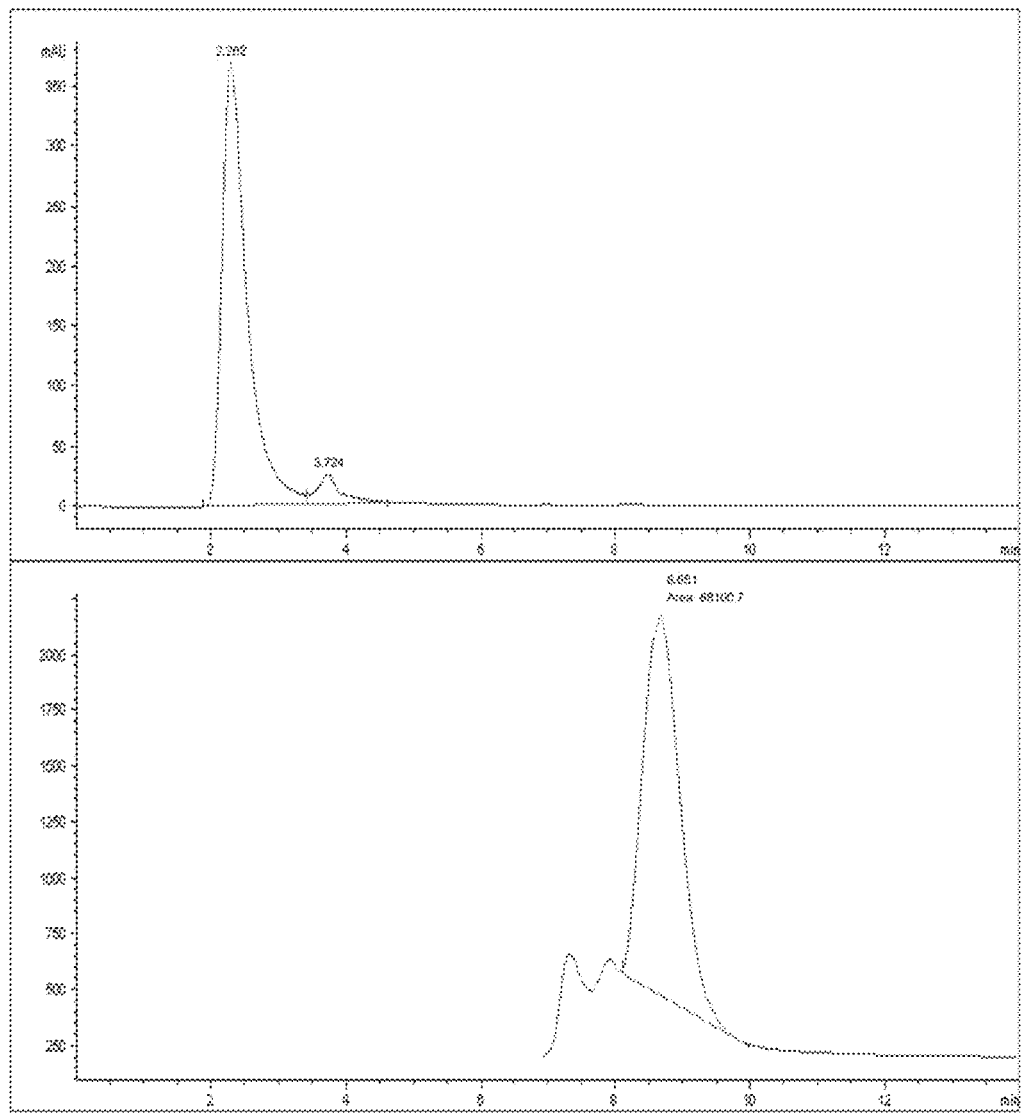
FIG. 12 is a chromatogram of prednisone in serum (2.5 ng/μl) run through an albumin column according to one aspect of the present invention.
Figure 13:
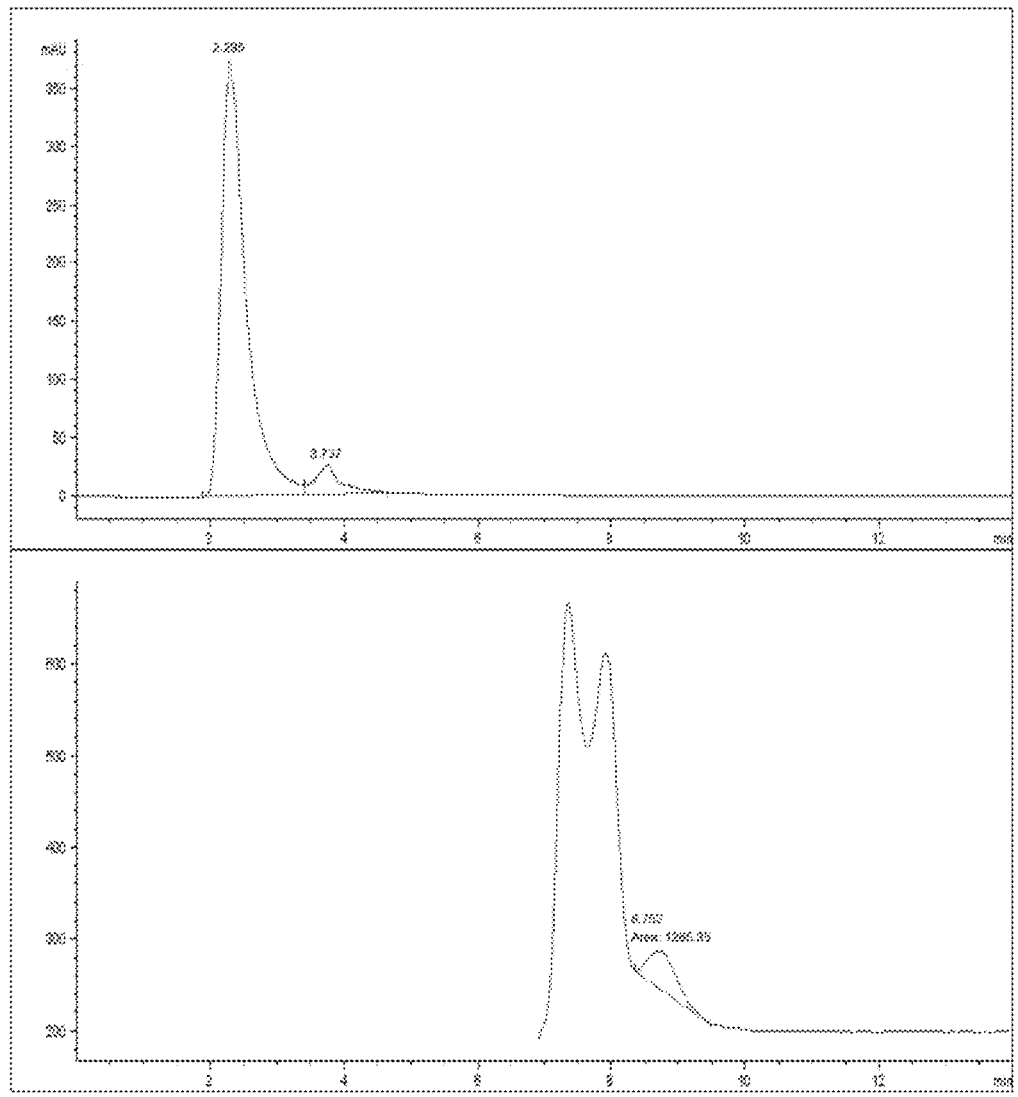
FIG. 13 is a chromatogram of prednisone in serum (0.05 ng/μl) run through an albumin column according to one aspect of the present invention.
Figure 14:
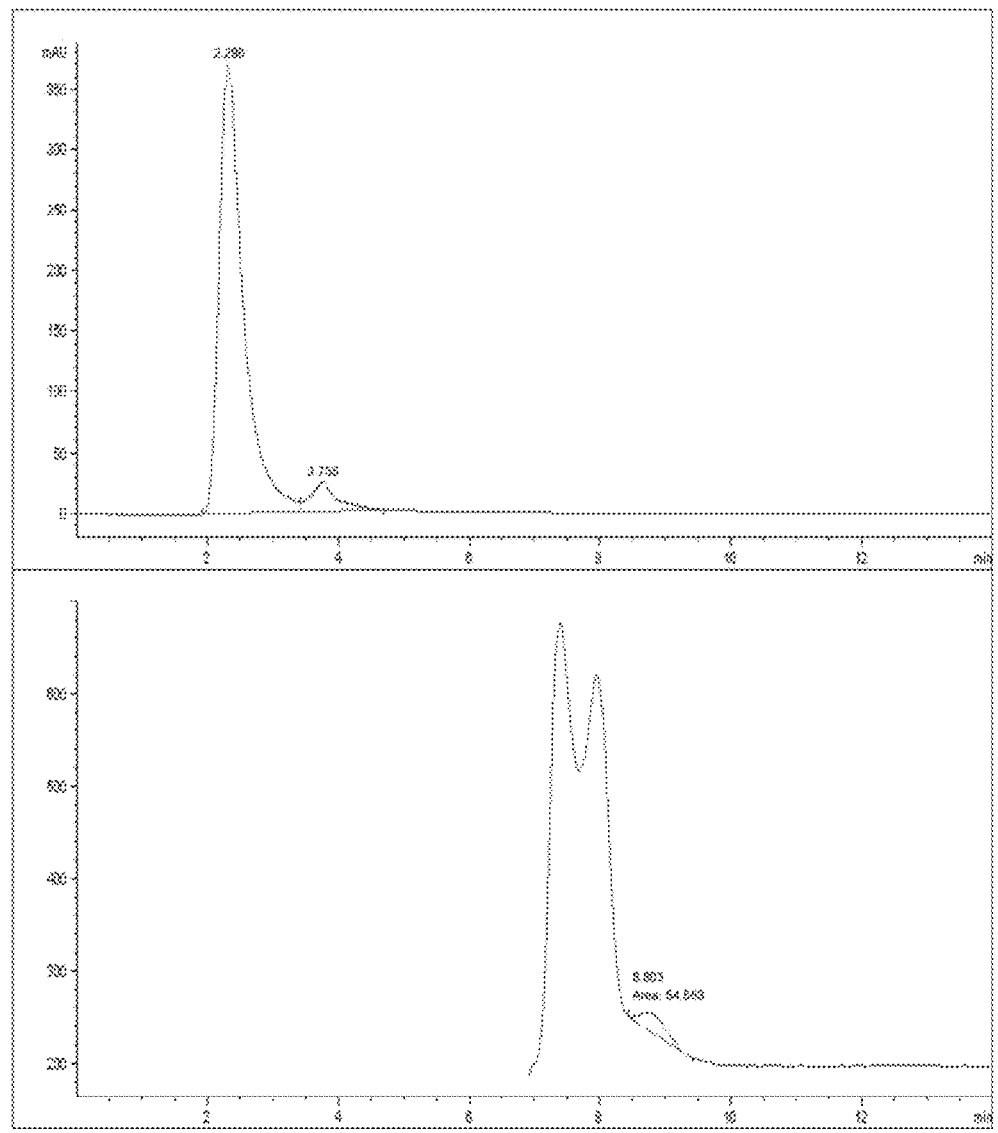
FIG. 14 is a chromatogram of prednisone in serum (0.01 ng/μl) run through an albumin column according to one aspect of the present invention.
Figure 15:
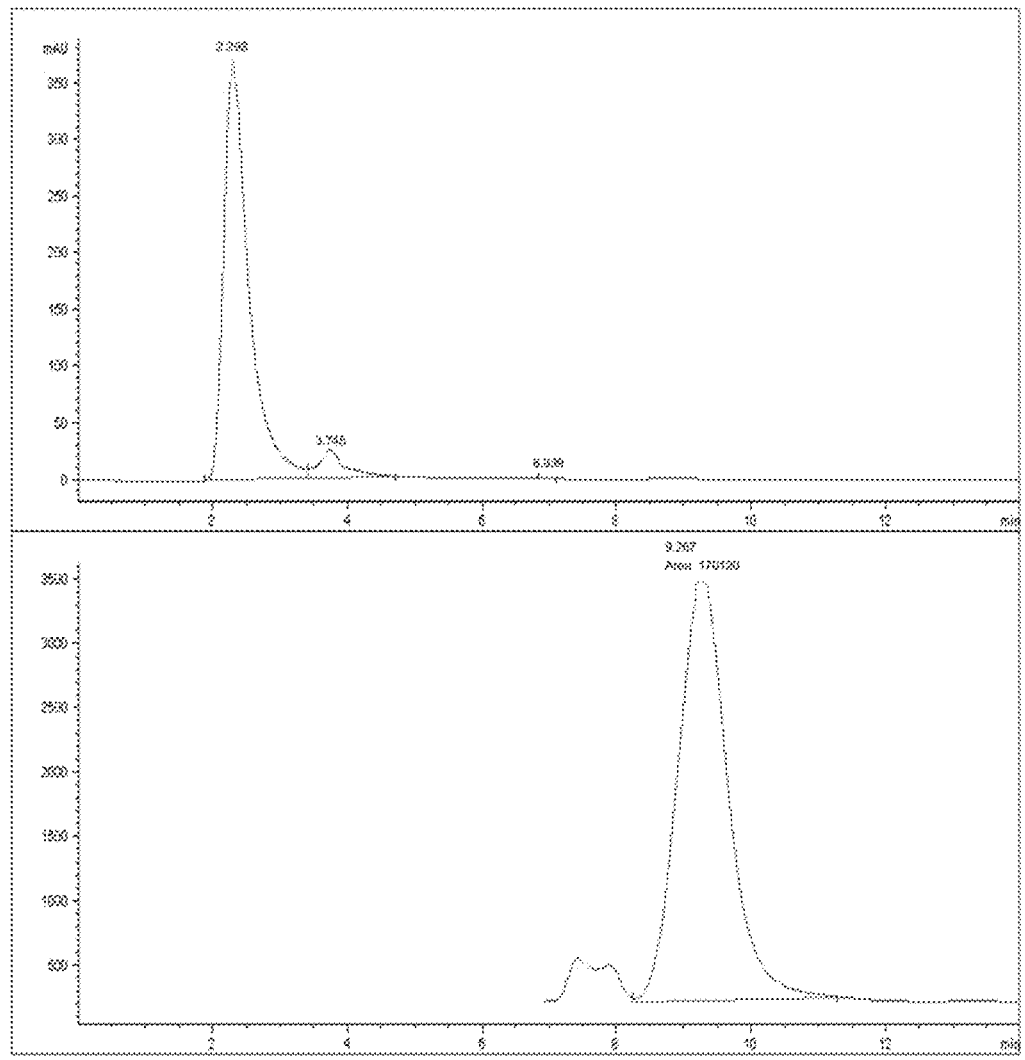
FIG. 15 is a chromatogram of prednisolone in serum (2.5 ng/μl) run through an albumin column according to one aspect of the present invention.
Figure 16:
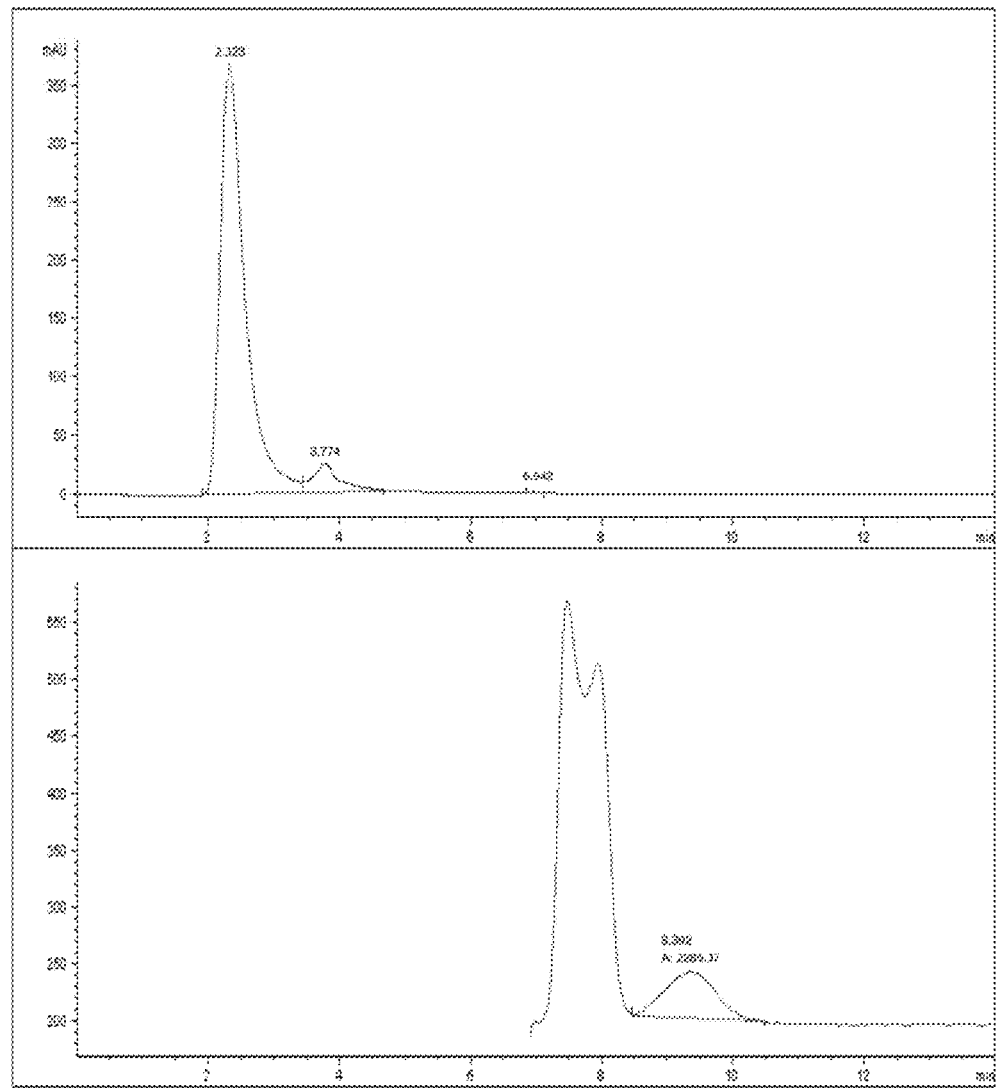
FIG. 16 is a chromatogram of prednisolone in serum (0.05 ng/μl) run through an albumin column according to one aspect of the present invention.
Figure 17:
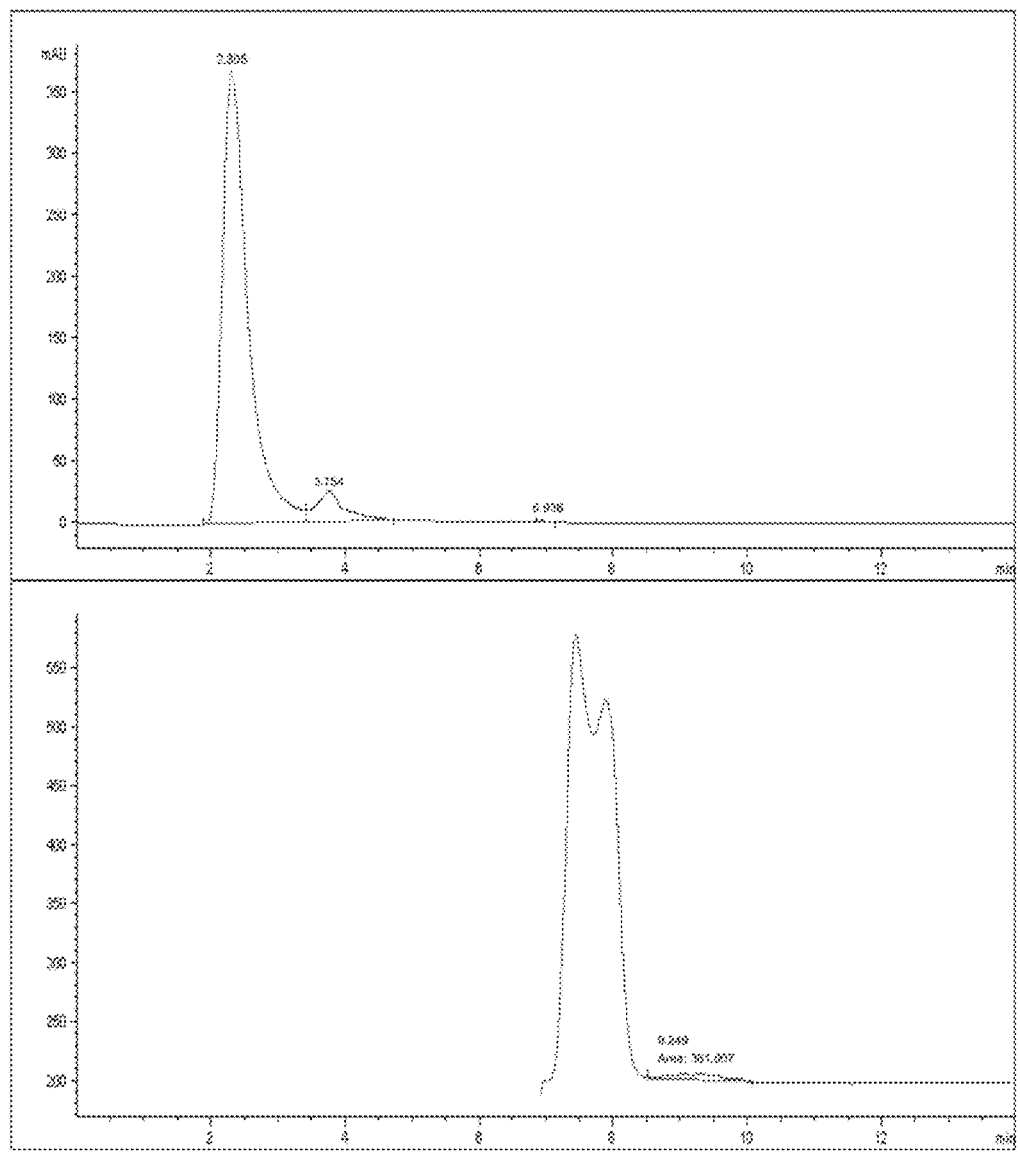
FIG. 17 is a chromatogram of prednisolone in serum (0.01 ng/μl) run through an albumin column according to one aspect of the present invention.
Figure 18:
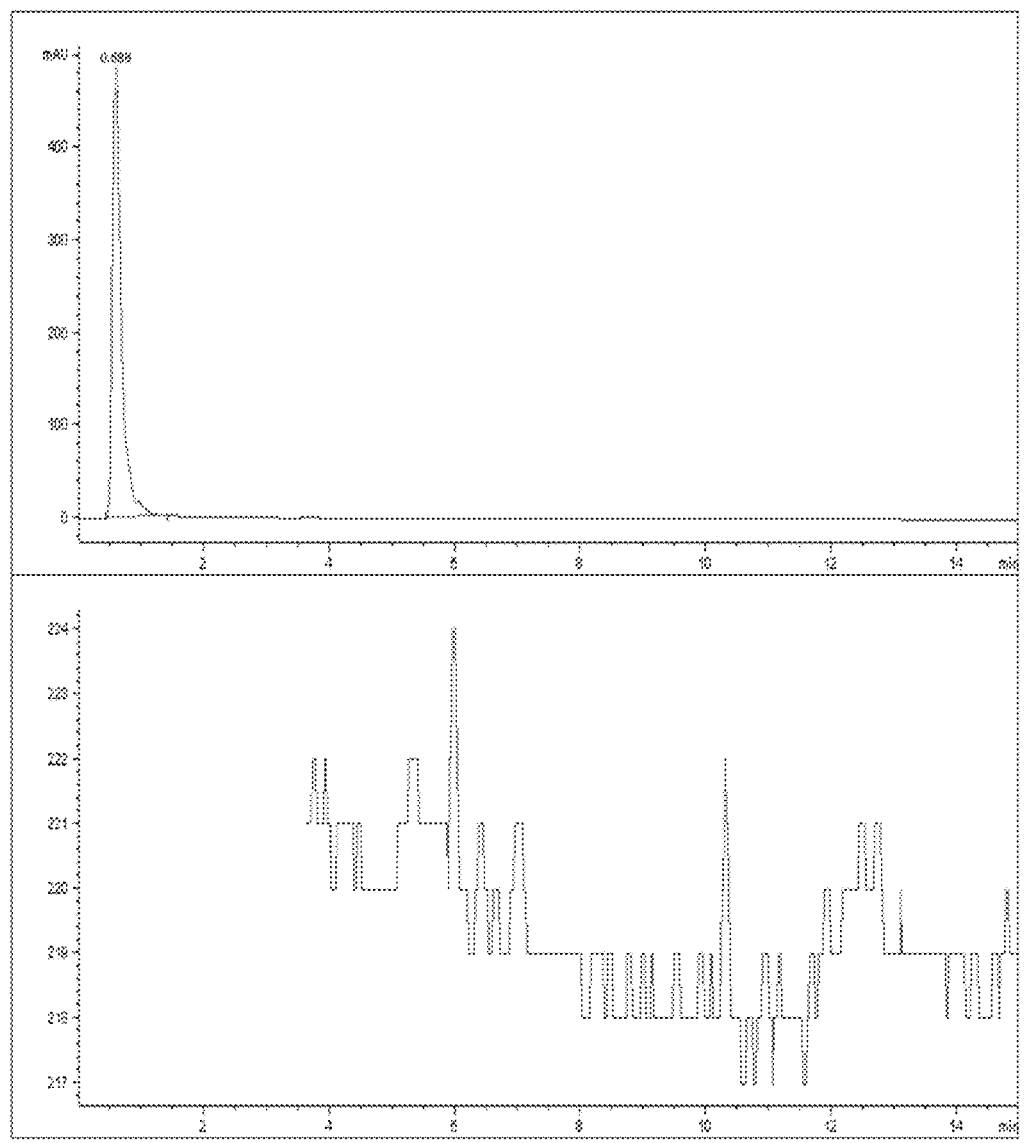
FIG. 18 is a chromatogram of n-serum (diluted 1:5 in a solvent buffer) run through an orosomucoid column according to one aspect of the present invention.
Figure 19:
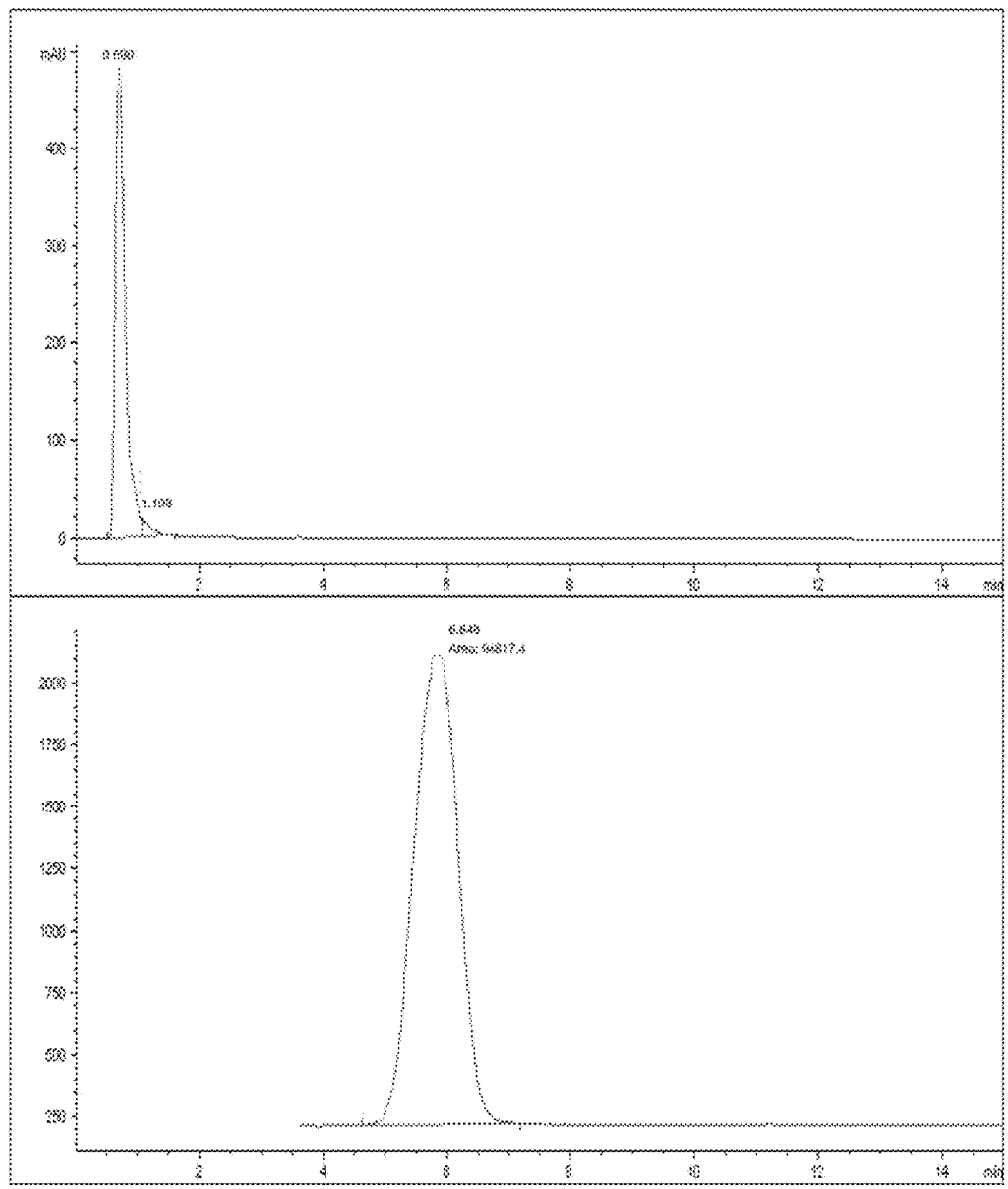
FIG. 19 is a chromatogram of cortisone in serum (2.5 ng/μl) run through an orosomucoid column according to one aspect of the present invention.
Figure 20:
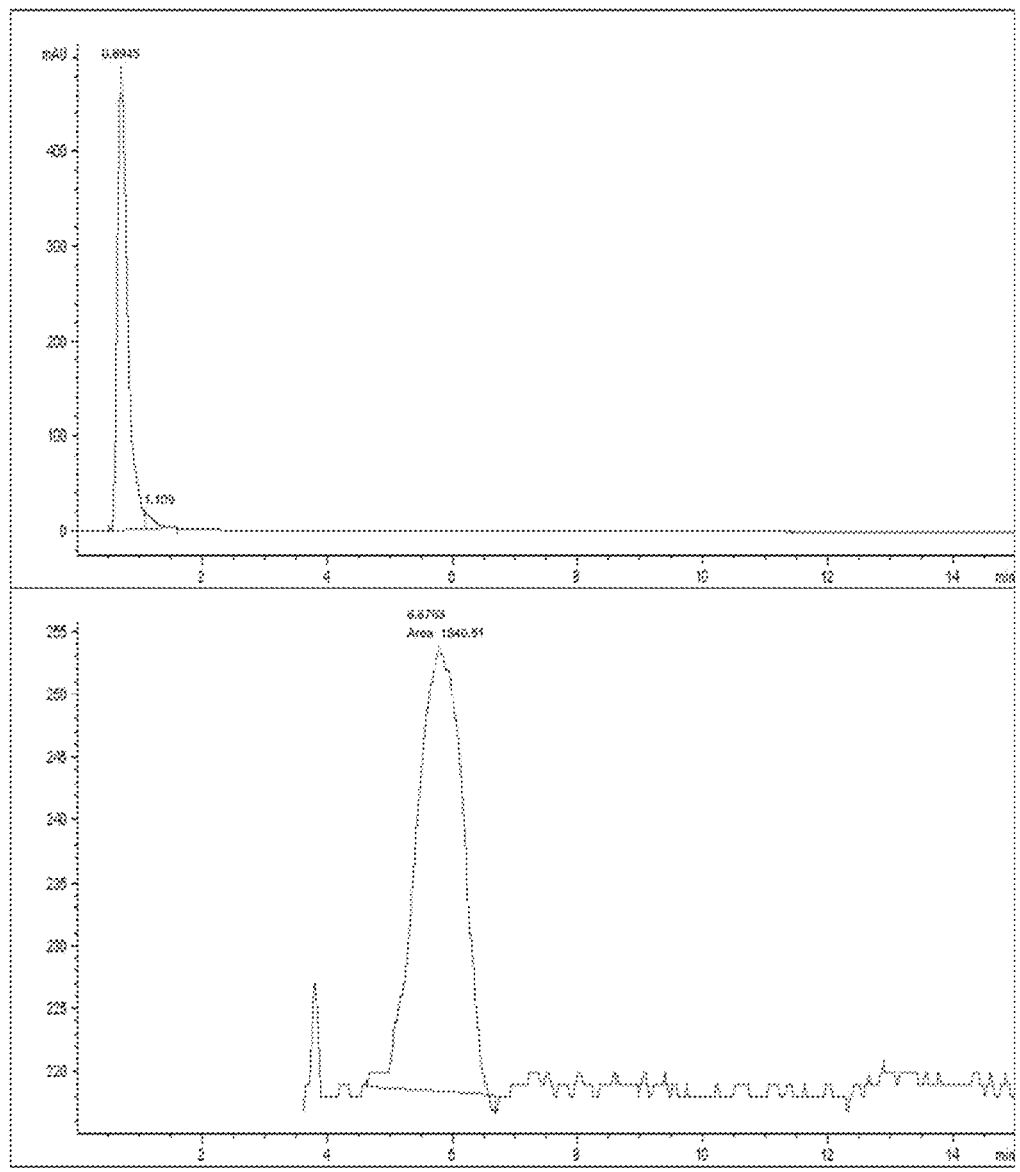
FIG. 20 is a chromatogram of cortisone in serum (0.05 ng/μl) run through an orosomucoid column according to one aspect of the present invention.
Figure 21:
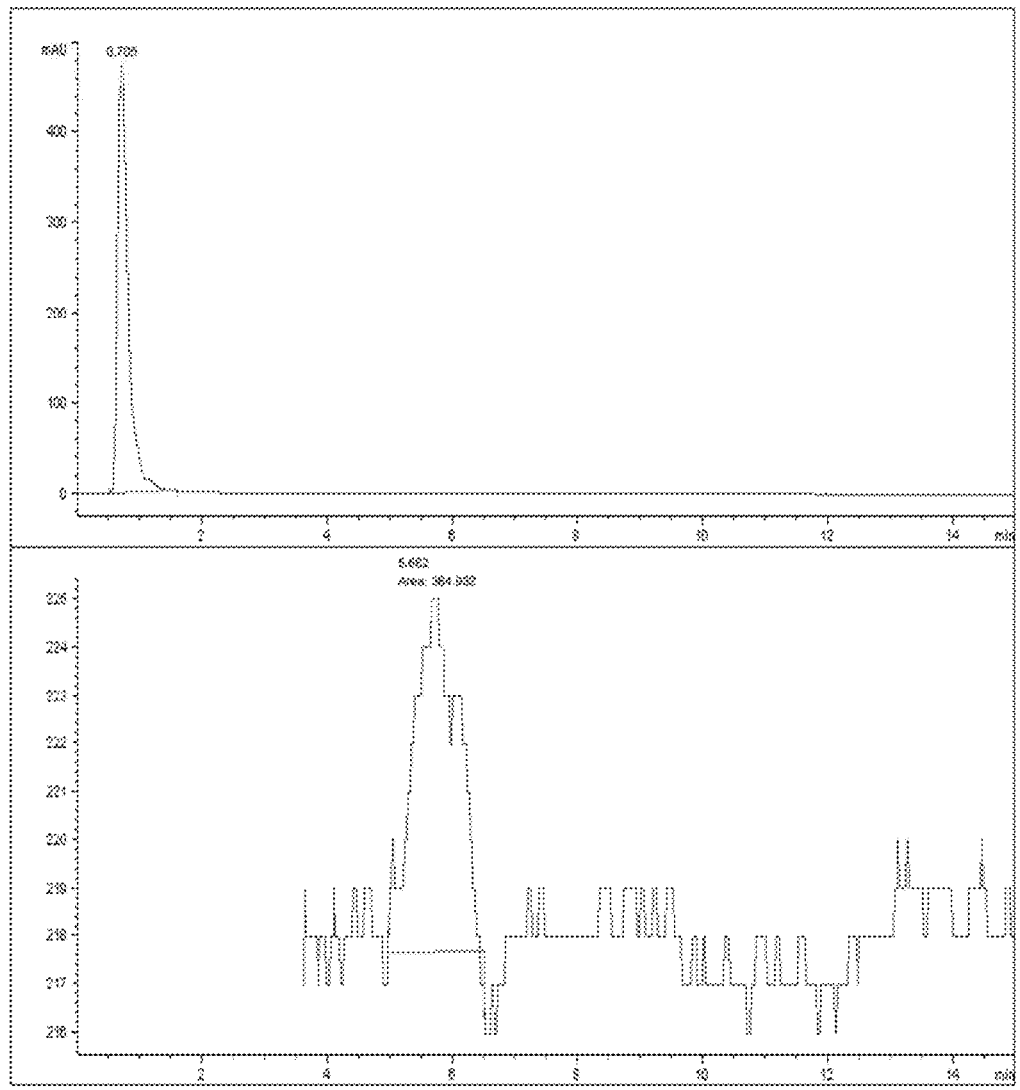
FIG. 21 is a chromatogram of cortisone in serum (0.01 ng/μl) run through an orosomucoid column according to one aspect of the present invention.
Figure 22:
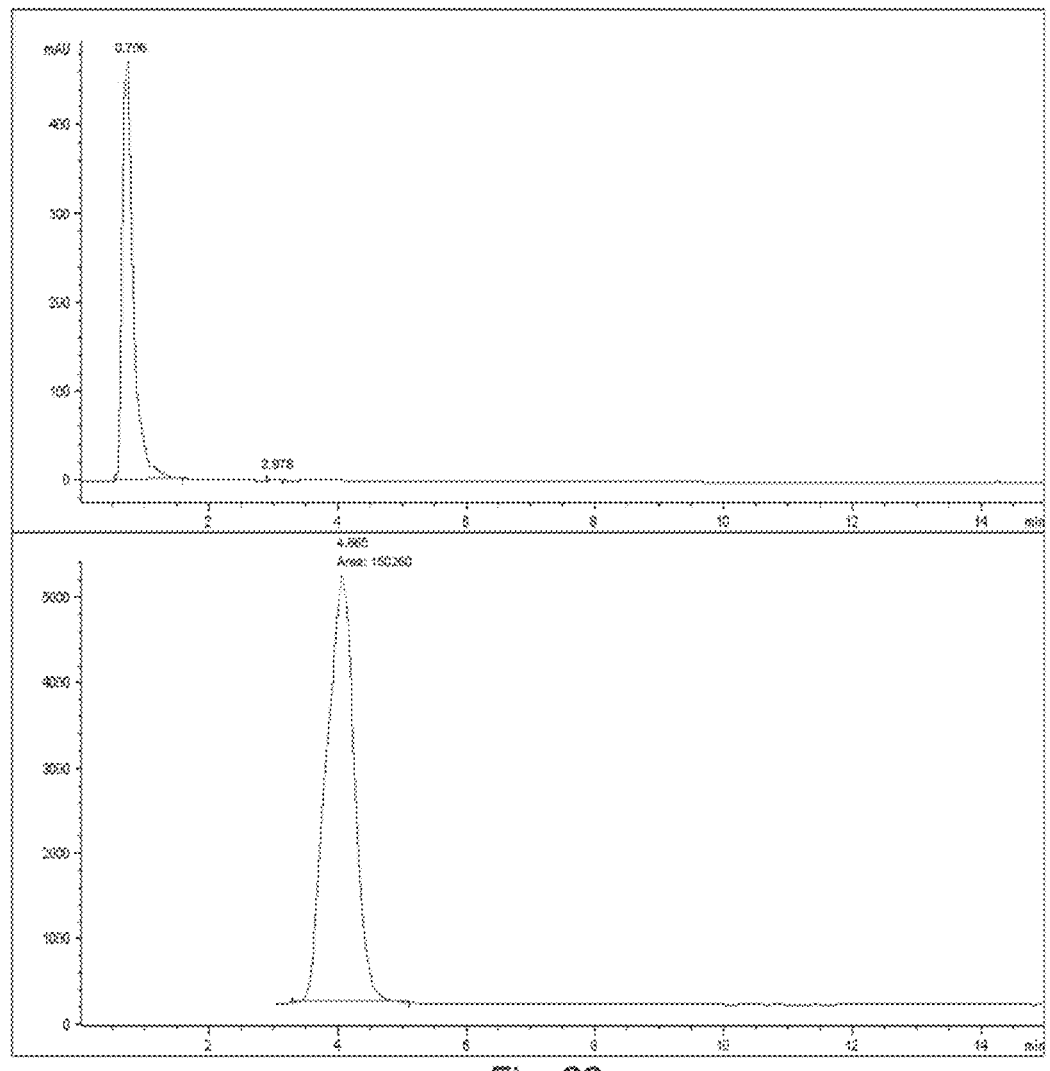
FIG. 22 is a chromatogram of hydrocortisone in serum (2.5 ng/μl) run through an orosomucoid column according to one aspect of the present invention.
Figure 23:
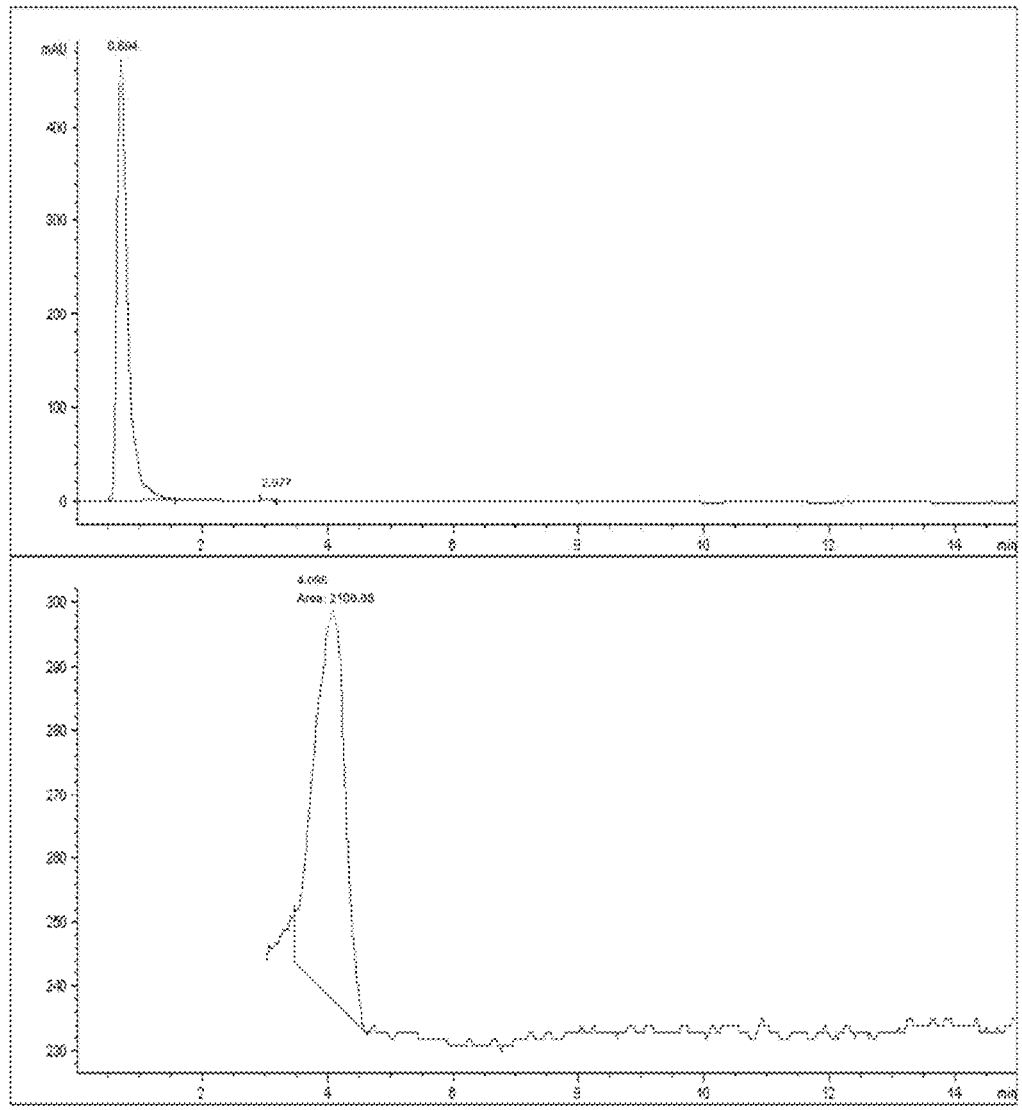
FIG. 23 is a chromatogram of hydrocortisone in serum (0.05 ng/μl) run through an orosomucoid column according to one aspect of the present invention.
Figure 24:
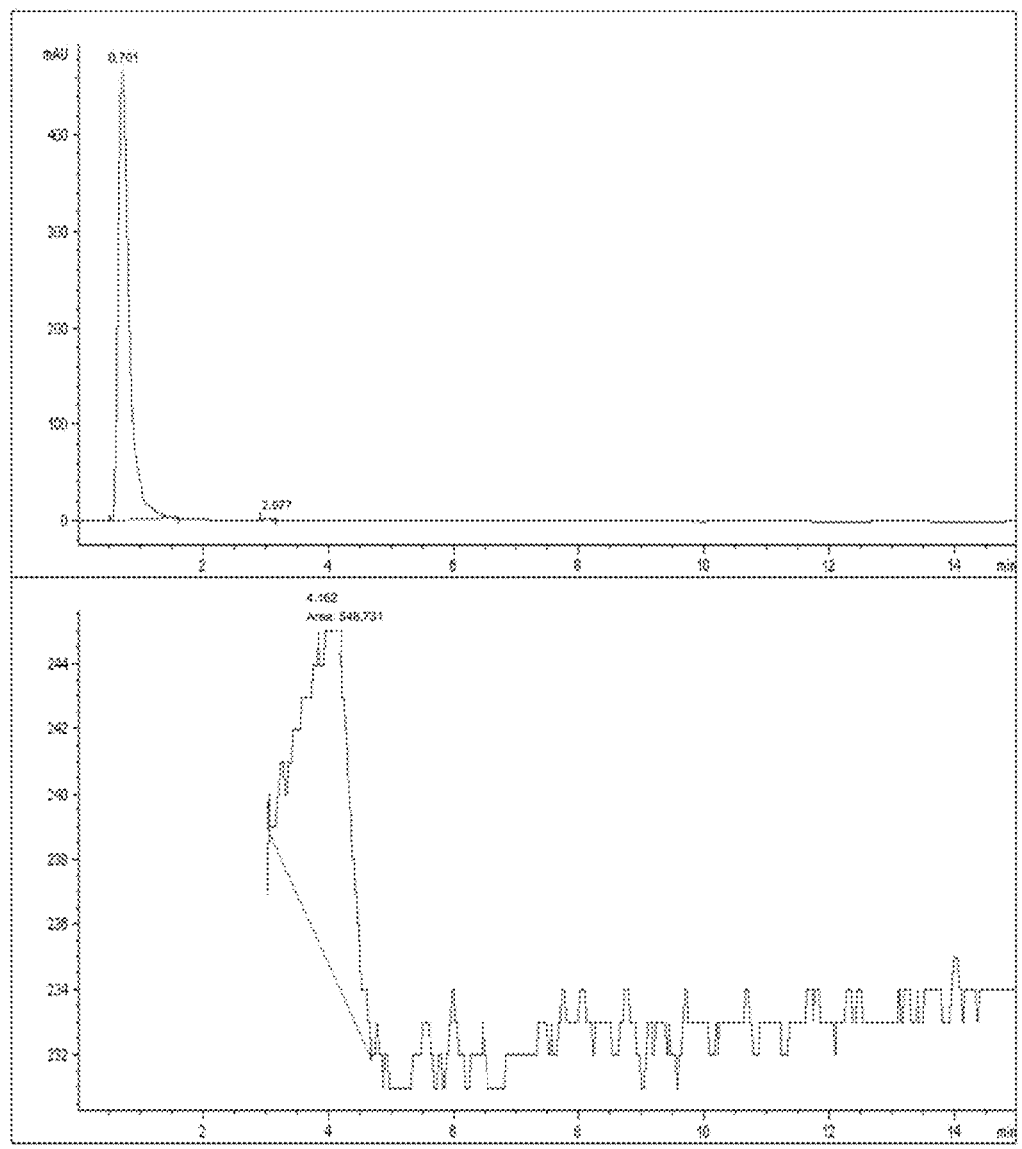
FIG. 24 is a chromatogram of hydrocortisone in serum (0.01 ng/μl) run through an orosomucoid column according to one aspect of the present invention.
Figure 25:
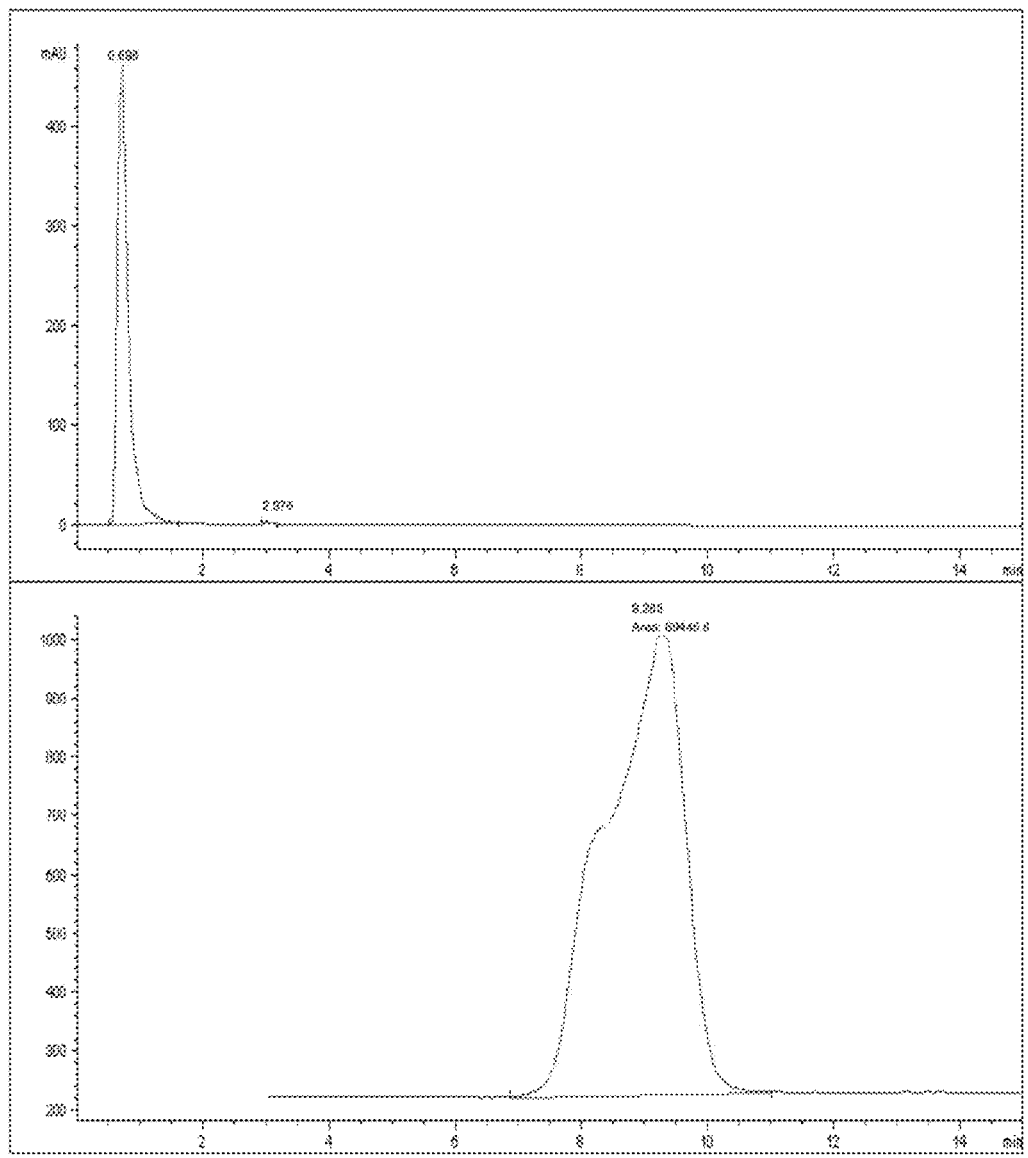
FIG. 25 is a chromatogram of prednisone in serum (2.5 ng/μl) run through an orosomucoid column according to one aspect of the present invention.
Figure 26:
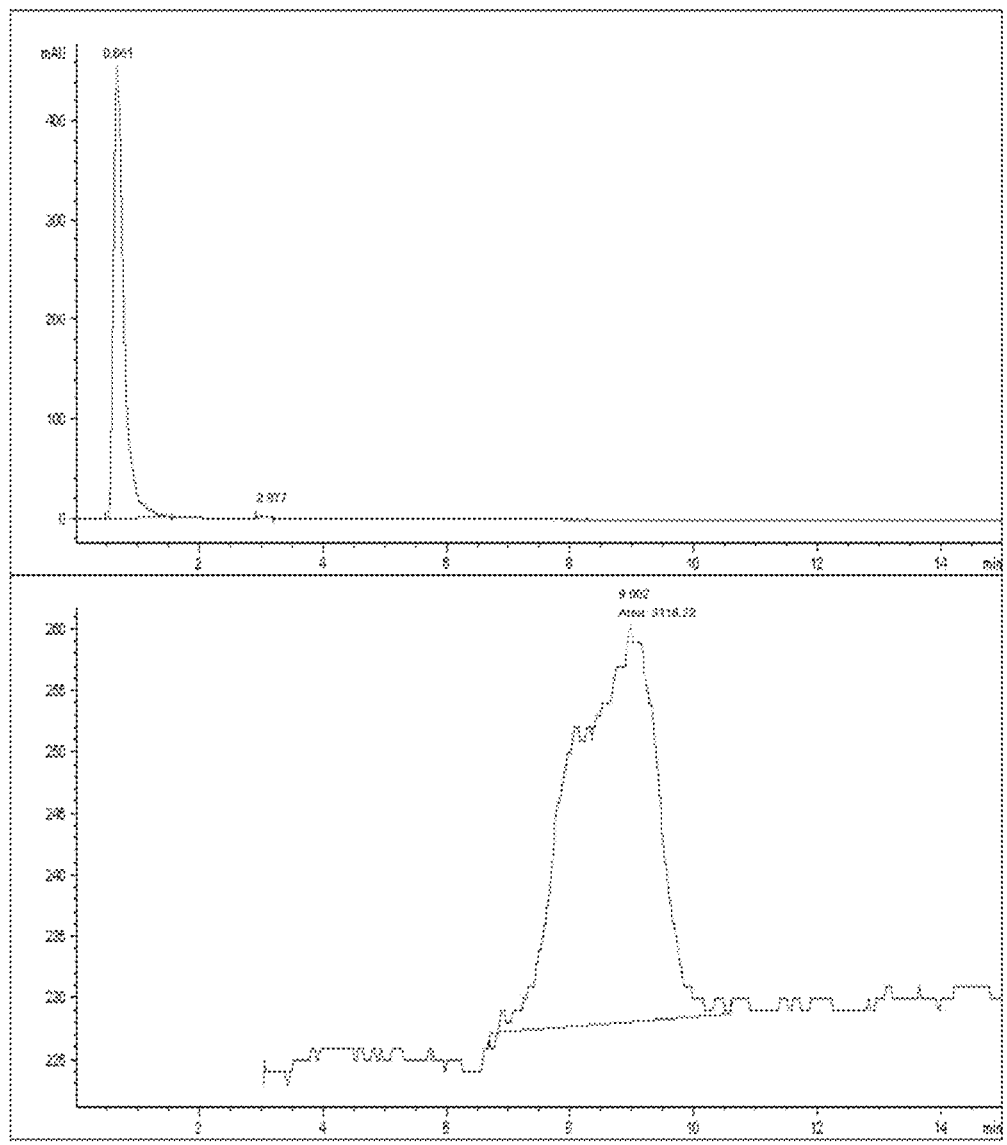
FIG. 26 is a chromatogram of prednisone in serum (0.05 ng/μl) run through an orosomucoid column according to one aspect of the present invention.
Figure 27:
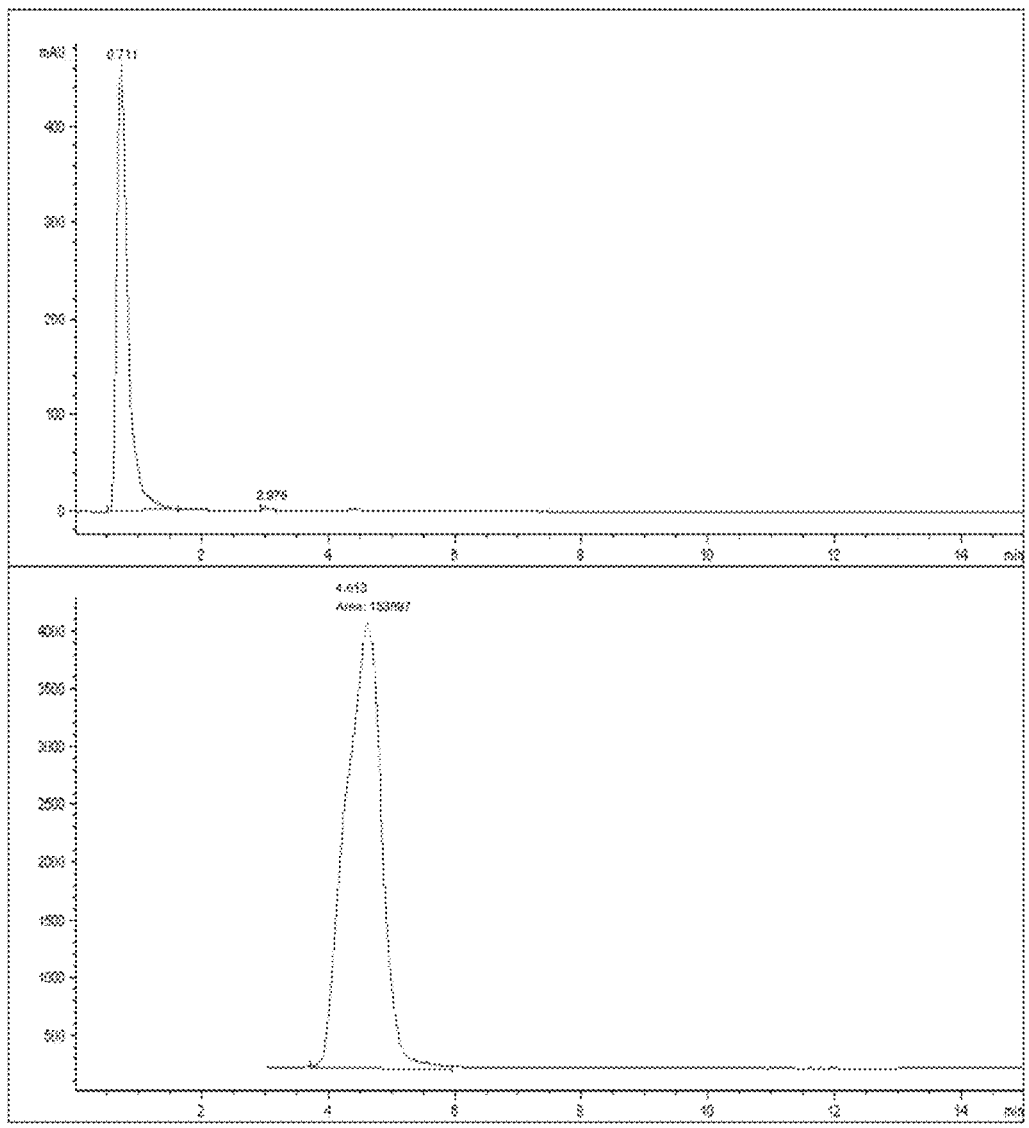
FIG. 27 is a chromatogram of prednisolone in serum (2.5 ng/μl) run through an orosomucoid column according to one aspect of the present invention.
Figure 28:
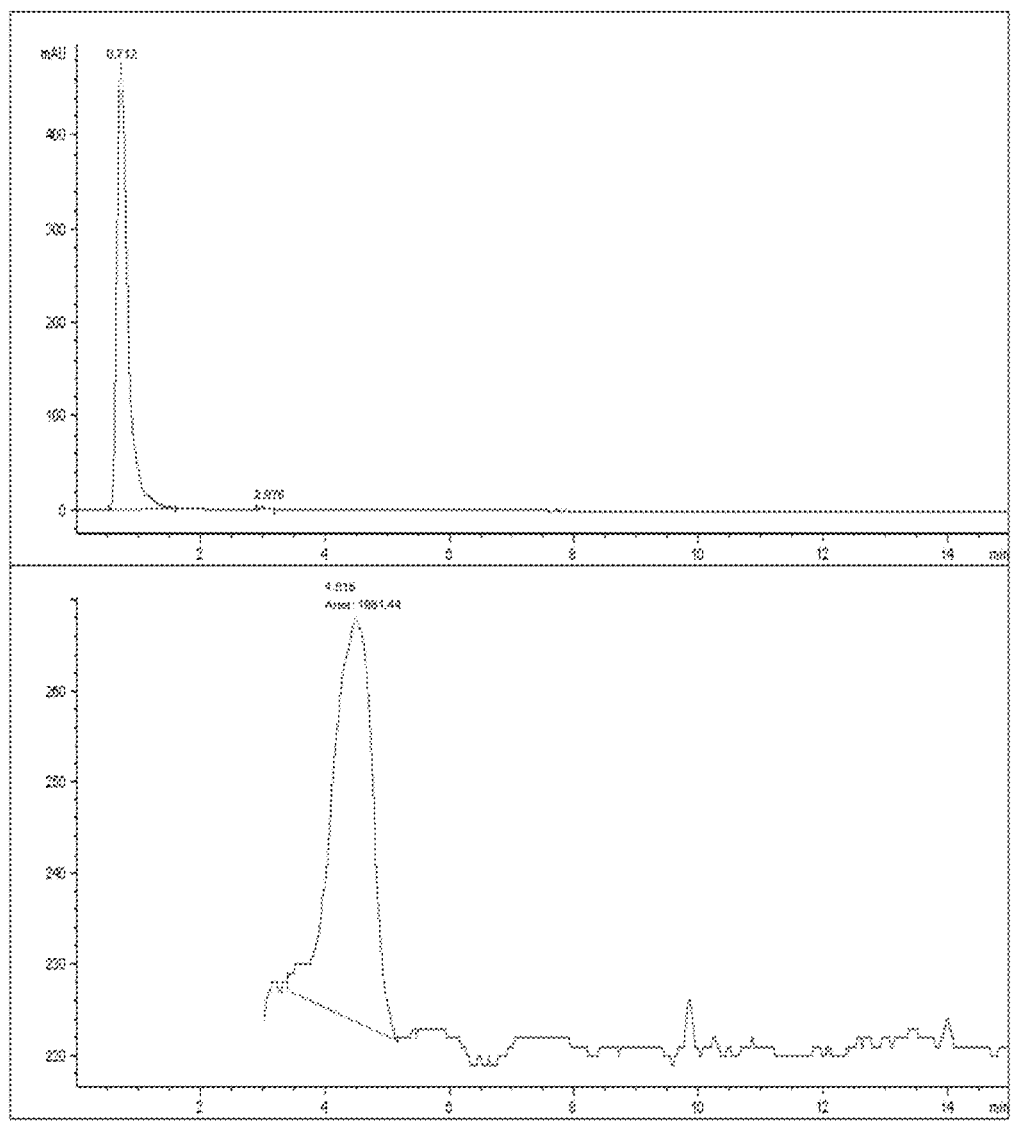
FIG. 28 is a chromatogram of prednisolone in serum (0.05 ng/μl) run through an orosomucoid column according to one aspect of the present invention.

Column C of Example 1 was loaded with n-Serum (pool from healthy volunteers) to determine elution time. Specifically, 2 µl of diluted n-serum, 1:10 with PBS was injected on column C, to see protein-level remaining on the column, as compared to elution time of steroids. A chromatogram of the serum on column C is shown in FIG. 4.

The serum peak eluted with the void of the column. At about 0.58 min, approximately 95% of the serum proteins eluted. Based on the chromatogram and examples provided herein, the steroids general appear at about 1.5-1.8 minutes. As such, the present columns can be used to separate steroids from serum and can be combined with mass spectrometry for subsequent detection.

Example 4

Column Preparation

Two columns were prepared. A BSA column was packed with silica (7 μm, 300 Å porosity) and loaded with 99% purity bovine serum albumin (BSA) at a concentration of 77.6 mg of BSA per gram of silica. A Orosomucoid column was packed with silica (7 μm, 300 Å porosity) and loaded with 99% purity orosomucoid at a concentration of 29.3 mg of orosomucoid per gram of silica. Both columns had dimensions of 50×2.1 mm stainless steel. Immobilization of the ligands was performed batchwise with periodate activation. 0.5 g of diol-silica (7 μm, 300 Å, Genesis) was used with 5 ml of $H_2O$ added. The silica was sonicated for 2 minutes, and 0.5 g of periodic acid was added to convert the diol groups to aldehyde groups. After 2 hours of mixing, the aldehyde-silica was washed with 100 mM phosphate, pH 7. 0.5 ml of the respective ligand in 100 mM phosphate buffer, pH 7.0, was prepared. Ligand concentration was 10 mg/ml. 250 μl $NaCNBH_3$, concentration of 0.1 mg/ml, was added. Coupling time was 40 hours at room temperature (22° C.) on mixing table. Ligand densities were calculated from measuring remaining BSA or orosomucoid levels in the supernatants and washings.

Example 5

Detection of Steroids in Serum

Four steroids, cortisone, hydrocortisone, prednisone, and prednisolone were tested on the columns of Example 4. The system comprised of the columns used in an Agilent 1200-LC-MS system. Solvent buffer was 10 mM ammonium-acetate (Am-Ac), pH 7.4. Column temperature was 22.5° C. with a flow rate of 0.100 ml/min for BSA column and flow rate of 0.200 ml/min for orosomucoid column. Detection included the use of diode-array detector (DAD) at 242 nm and mass spectroscopy with electrospray (ES)—atmospheric pressure ionization (API) selective ion monitoring (SIM) for molecular weights of 358 (prednisone), 360 (cortisone, prednisolone), and 362 (hydrocortisone), total ion chromatograms (TIC). To avoid interference with serum, a delay was set to 6.9 minutes for the BSA column and 3.9 minutes for the Orosomucoid column.

The steroids were all dissolved in solvent buffer at a concentration of 200 ng/μl. N-serum was diluted 1:5 with solvent buffer. Spiked serum samples were made by adding steroids to the diluted serum, and three further dilutions with diluted serum. Concentrations ranged from 2.5 ng/μl to 0.01 ng/μl, of each steroid. 2 μl samples were run in duplicate. A spiked serum sample with high steroid concentration (12.5 ng/μl) was run on both columns.

Recovery, comparison between steroid spiked serum standards and steroids in solvent buffer. This was performed with the BSA-column only.

Tables 5-6 provide steroids on each column at varying concentrations and resulting findings.

TABLE 5

BSA Column

| Steroid | Conc. (ng/μl) | Total (ng) | Retention (min.) | Recovery (%) |
|---|---|---|---|---|
| Cortisone | 2.5 | 5 | 8.63 | 73 |
| Cortisone | 0.25 | 0.5 | 8.67 | 63 |
| Cortisone | 0.05 | 0.1 | 8.67 | 60 |
| Cortisone | 0.01 | 0.02 | 8.73 | 59 |
| Hydrocortisone | 2.5 | 5 | 8.44 | 71 |
| Hydrocortisone | 0.25 | 0.5 | 8.49 | 58 |
| Hydrocortisone | 0.05 | 0.1 | 8.50 | 41 |
| Hydrocortisone | 0.01 | 0.02 | 8.58 | 49 |
| Prednisone | 2.5 | 5 | 8.70 | 59 |
| Prednisone | 0.25 | 0.5 | 8.75 | 47 |
| Prednisone | 0.05 | 0.1 | 8.82 | 61 |
| Prednisone | 0.01 | 0.02 | 8.79 | 100 |
| Prednisolone | 2.5 | 5 | 9.27 | 99 |
| Prednisolone | 0.25 | 0.5 | 9.35 | — |
| Prednisolone | 0.05 | 0.1 | 9.39 | — |
| Prednisolone | 0.01 | 0.02 | 9.14 | — |

TABLE 6

Orosomucoid Column

| Steroid | Conc. (ng/μl) | Total (ng) | Retention (min.) |
|---|---|---|---|
| Cortisone | 2.5 | 5 | 5.85 |
| Cortisone | 0.25 | 0.5 | 5.88 |
| Cortisone | 0.05 | 0.1 | 5.76 |
| Cortisone | 0.01 | 0.02 | 5.66 |
| Hydrocortisone | 2.5 | 5 | 4.06 |
| Hydrocortisone | 0.25 | 0.5 | 4.07 |
| Hydrocortisone | 0.05 | 0.1 | 3.98 |
| Hydrocortisone | 0.01 | 0.02 | 4.16 |
| Prednisone | 2.5 | 5 | 9.29 |
| Prednisone | 0.25 | 0.5 | 9.29 |
| Prednisone | 0.05 | 0.1 | 9.02 |
| Prednisone | 0.01 | 0.02 | — |
| Prednisolone | 2.5 | 5 | 4.61 |
| Prednisolone | 0.25 | 0.5 | 4.37 |
| Prednisolone | 0.05 | 0.1 | 4.52 |
| Prednisolone | 0.01 | 0.02 | 3.90 |

FIGS. 5-17 show chromatograms on an albumin column from example 4 for the serum (1:5 dilution in buffer), cortisone (2.5 ng/μl, 0.05 ng/μl, 0.01 ng/μl), hydrocortisone (2.5 ng/μl, 0.05 ng/μl, 0.01 ng/μl), prednisone (2.5 ng/μl, 0.05 ng/μl, 0.01 ng/μl), and prednisolone (2.5 ng/μl, 0.05 ng/μl, 0.01 ng/μl), respectively.

FIGS. 18-29 show chromatograms on an orosomucoid column from example 4 for the serum (1:5 dilution in buffer), cortisone (2.5 ng/μl, 0.05 ng/μl, 0.01 ng/μl), hydrocortisone (2.5 ng/μl, 0.05 ng/μl, 0.01 ng/μl), prednisone (2.5 ng/μl, 0.05 ng/μl, 0.01 ng/μl), and prednisolone (2.5 ng/μl, 0.05 ng/μl), respectively.

Figure 29:
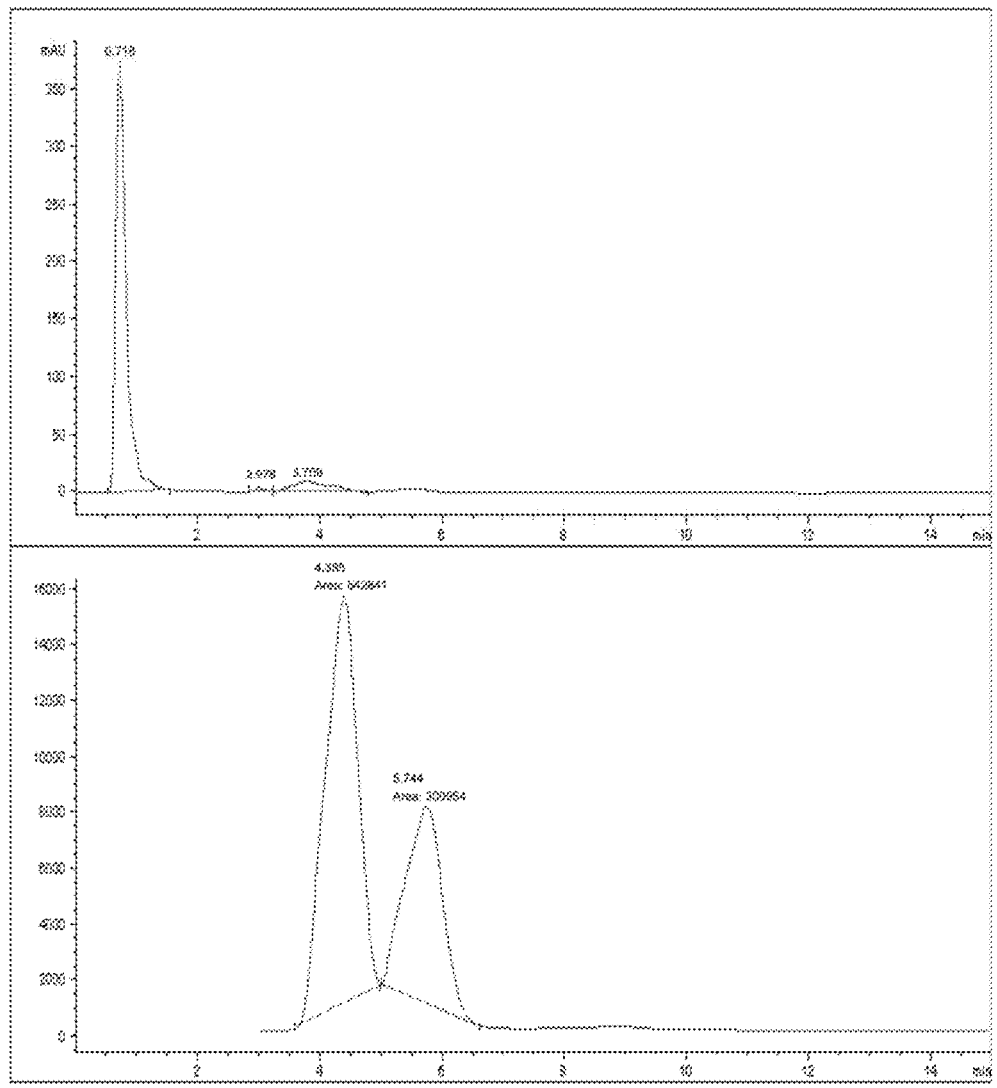
FIG. 29 is a chromatogram of a steroid mix (cortisone, hydrocortisone, prednisone, and prednisolone) at a concentration of 12.5 ng/μl run through an orosomucoid column according to one aspect of the present invention.
Figure 30:
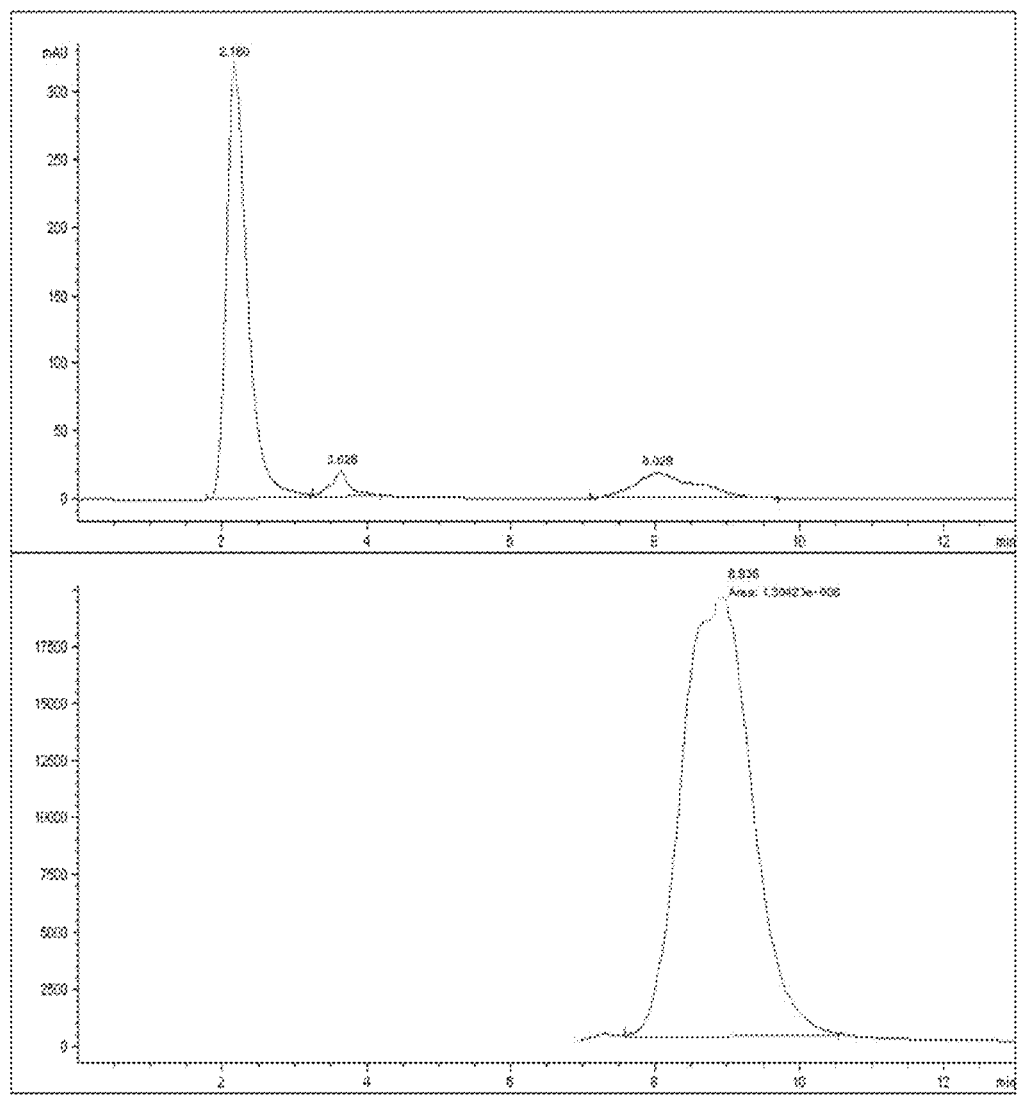
FIG. 30 is a chromatogram of for a steroid mix (cortisone, hydrocortisone, prednisone, and prednisolone) at a concentration of 12.5 ng/μl run through an albumin column according to one aspect of the present invention.

FIGS. 29-30 show chromatograms for the steroid mix (cortisone, hydrocortisone, prednisone, and prednisolone) at a concentration of 12.5 ng/μl on the Orosomucoid column and the BSA column, respectively.

Figure 31:
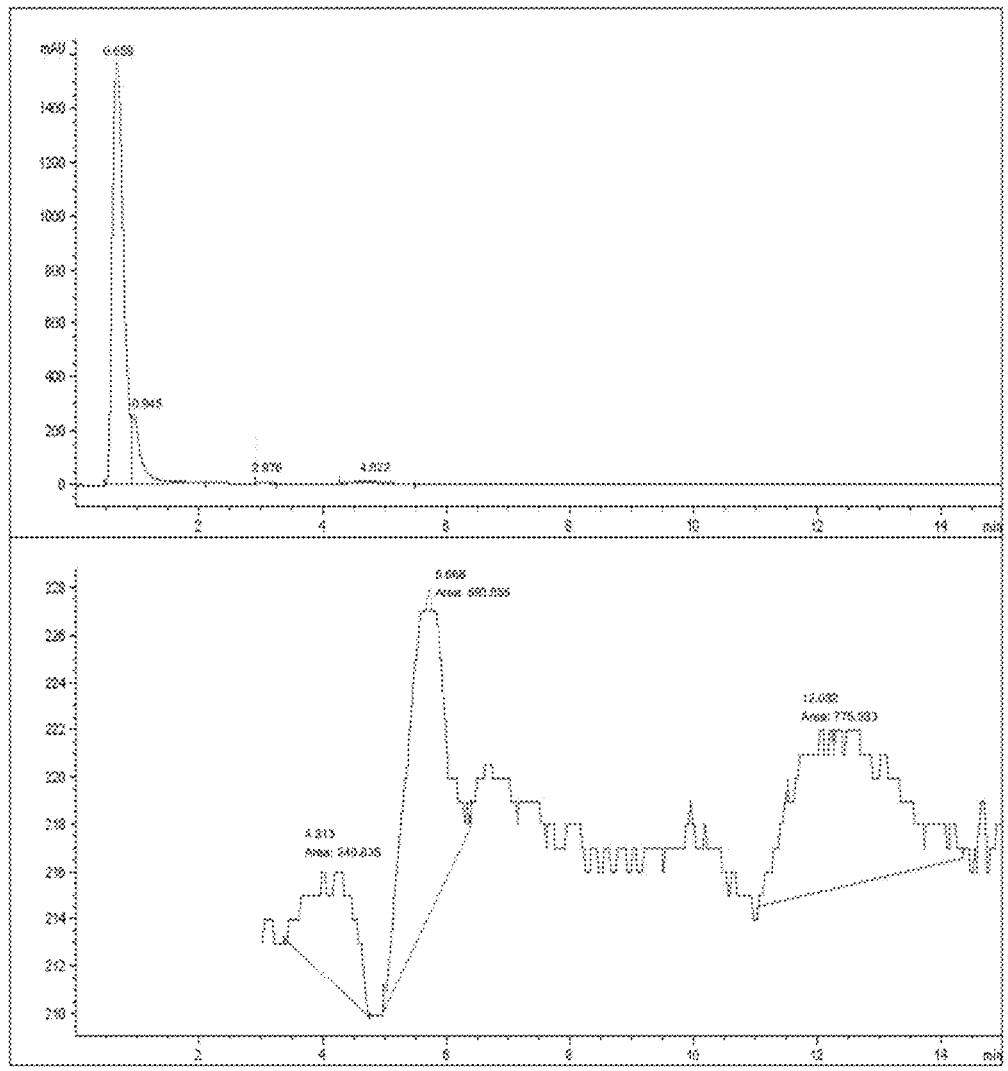
FIG. 31 is a chromatogram of n-serum undiluted run through an orosomucoid column according to one aspect of the present invention.

FIG. 31 shows a chromatogram of n-serum undiluted on the orosomucoid column.

Notably, the steroids could be detected in serum down to a detection limit of 10-50 pg/μl of diluted serum or even less. As such, it is possible to detect native steroids present in normal serum samples.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method for detecting and analyzing a target compound in a biological sample, comprising:
    delivering a biological sample through an affinity column, the affinity column having a binding ligand coupled to a stationary structural support, wherein the affinity column has a density of at least 25 mg/g of the binding ligand per the stationary structural support and wherein the binding ligand has been preselected to cause weak affinity separation zonal retardation of the target compound from the biological sample forming a target compound fraction and a biological sample fraction; and
    detecting whether the target compound is present in the target compound fraction by mass spectrometry wherein the target compound is a steroid.

2. The method of claim 1, wherein the binding ligand is a protein.

3. The method of claim 2, wherein the protein is selected from the group consisting of: transferrin, immunoglobulin, albumin, fibrinogen, orosomucoid, and mixtures thereof.

4. The method of claim 2, wherein the protein is albumin.

5. The method of claim 1, wherein the target compound is a small molecule having a molecular weight of less than 500.

6. The method of claim 1, wherein the steroid is selected from the group consisting of cortisone, hydrocortisone, prednisone, prednisolone, adrenal steroids, estradiol, testosterone, secosteroids, vitamin D derivatives, and mixtures thereof.

7. The method of claim 1, wherein the biological sample is selected from the group consisting of blood serum, blood plasma, urine, CNS fluid, saliva, cellular extracts, tissue culture extracts, and mixtures thereof.

8. The method of claim 5, further comprising treating the biological sample with a reducing agent, a protease enzyme treatment, a carbohydrate modification, a detergent, urea, or a combination thereof.

9. The method of claim 5, wherein the biological sample is blood serum, blood plasma, or urine.

10. The method of claim 1, wherein the biological sample is an undiluted biological fluid.

11. The method of claim 1, wherein the biological sample is a non-dialyzed biological fluid.

12. The method of claim 1, wherein the biological sample is a non-ultrafiltrated biological fluid.

13. The method of claim 1, wherein the binding ligand has a density of at least 50 mg/g.

14. The method of claim 1, wherein the biological sample contains additional binding ligands.

15. The method of claim 14, wherein the additional binding ligands are present in the biological sample in an amount ranging from about 1 g/dL to about 10 g/dL.

16. The method of claim 1, wherein the target compound is present in the biological sample in an amount ranging from about 1 pg/µl to about 10 µg/µl.

17. The method of claim 1, wherein the target compound is present in the biological sample in an amount ranging from about 10 pg/µl to about 1 µg/µl.

18. The method of claim 1, wherein the high density of binding ligands of the affinity column is sufficient to cause weak affinity separation zonal retardation when the biological sample contains additional binding ligands.

* * * * *